(12) United States Patent
Vermeiren et al.

(10) Patent No.: US 11,124,708 B2
(45) Date of Patent: Sep. 21, 2021

(54) PROCESS FOR THE PRODUCTION OF HIGH VALUE CHEMICALS FROM BIOLOGICALLY PRODUCED MATERIALS

(71) Applicant: Total Research & Technology Feluy, Seneffe (BE)

(72) Inventors: Walter Vermeiren, Houthalen (BE); Valérie Vanrysselberghe, Aalbeke (BE)

(73) Assignee: Total Research & Technology Feluy, Seneffe (BE)

( * ) Notice: Subject to any disclaimer, the term of this patent is extended or adjusted under 35 U.S.C. 154(b) by 0 days.

(21) Appl. No.: 15/518,007

(22) PCT Filed: Oct. 9, 2015

(86) PCT No.: PCT/EP2015/073455
§ 371 (c)(1),
(2) Date: Apr. 10, 2017

(87) PCT Pub. No.: WO2016/058953
PCT Pub. Date: Apr. 21, 2016

(65) Prior Publication Data
US 2017/0298280 A1 Oct. 19, 2017

(30) Foreign Application Priority Data
Oct. 13, 2014 (EP) .................................. 14188696

(51) Int. Cl.
*C10G 9/36* (2006.01)
*C07C 4/04* (2006.01)
(Continued)

(52) U.S. Cl.
CPC ................. *C10G 9/36* (2013.01); *C01B 3/24* (2013.01); *C07C 4/04* (2013.01); *C10G 3/46* (2013.01);
(Continued)

(58) Field of Classification Search
CPC .... C10G 9/36; C10G 3/50; C10G 3/46; C07C 4/04
See application file for complete search history.

(56) References Cited

U.S. PATENT DOCUMENTS 3,923,921 A * 12/1975 Kohfeldt ................ B01D 51/10
208/100
2011/0319683 A1  12/2011  Abhari et al.
(Continued)

FOREIGN PATENT DOCUMENTS

CN  101723783 A  6/2010
EP  2290035 A1  3/2011
(Continued)

OTHER PUBLICATIONS

Melpolder et al. (Composition of naphtha from fluid catalytic cracking, 1952, Industrial and engineering chemistry, vol. 44, No. 5, pp. 1142-1146) (Year: 1952).*
(Continued)

*Primary Examiner* — Youngsul Jeong
(74) *Attorney, Agent, or Firm* — Albert Shung

(57) ABSTRACT

The present invention relates to a process for the production of high value chemicals, preferably including at least ethylene and propylene, by steam cracking a mixture of non-cyclic paraffin stream (A) comprising at least 90% of components having at least 12 carbon atoms, with either a mixture of hydrocarbons having from 3 to 4 carbon atoms or a mixture of hydrocarbons comprising at least 90% of components having a boiling point ranging from 15° C. to 200° C.

20 Claims, 6 Drawing Sheets

(51) Int. Cl.
*C10G 3/00* (2006.01)
*C01B 3/24* (2006.01)

(52) U.S. Cl.
CPC ........ *C10G 3/50* (2013.01); *C01B 2203/0272* (2013.01); *C01B 2203/065* (2013.01); *C10G 2300/104* (2013.01); *C10G 2300/1011* (2013.01); *C10G 2300/1044* (2013.01); *C10G 2300/1051* (2013.01); *C10G 2300/1055* (2013.01); *C10G 2300/1081* (2013.01); *C10G 2300/202* (2013.01); *C10G 2400/20* (2013.01); *C10G 2400/30* (2013.01); *Y02P 20/52* (2015.11); *Y02P 30/20* (2015.11)

(56) References Cited

U.S. PATENT DOCUMENTS

| | | | |
|---|---|---|---|
| 2012/0142983 A1* | 6/2012 | Vermeiren | C11B 3/06 585/240 |
| 2013/0261362 A1* | 10/2013 | Fingland | B01J 23/002 585/324 |
| 2014/0046103 A1 | 2/2014 | Abhari et al. | |

FOREIGN PATENT DOCUMENTS

| | | |
|---|---|---|
| EP | 2290045 A1 | 3/2011 |
| FR | 2917424 A1 | 12/2008 |
| WO | 2011012438 A1 | 2/2011 |
| WO | 2011012439 A1 | 2/2011 |
| WO | 2014093016 A1 | 6/2014 |
| WO | 2014111598 A2 | 7/2014 |

OTHER PUBLICATIONS

Da Vinci (Da Vinci Laboratory Solutions, The analysis of hydrocarbon composition in LPG by GC using the DVLS liquefied gas injector, 2015). (Year: 2015).*

International Search Report issued in PCT/EP2015/073455, dated Feb. 8, 2016, 4 pages.

Fréedérick Adam et al., "Towards Comprehensive Hydrocarbons Analysis of Middle Distillates by LC—GC×GC"; Journal of Chromatographic Science, vol. 45, Nov./Dec. 2007 pp. 643-649.

* cited by examiner

PROCESS FOR THE PRODUCTION OF HIGH VALUE CHEMICALS FROM BIOLOGICALLY PRODUCED MATERIALS

CROSS-REFERENCE TO RELATED APPLICATIONS

This application claims the benefit of PCT/EP2015/073455 filed Oct. 9, 2015, which claims priority from EP 14188696.0 filed Oct. 13, 2014.

FIELD OF THE INVENTION

The present invention relates to the production of high value chemicals such as ethylene, propylene, benzene, butadiene or hydrogen by steam cracking of paraffinic hydrocarbons. In particular, the invention relates to the production of high value chemicals from bio-based products, such as fatty acids or glycerides thereof.

BACKGROUND OF THE INVENTION

Brand owners are demanding for more renewable conventional plastics, pointing to the need for drop-in monomers like ethylene, propylene, butadiene and aromatics for making polymers. Alternative resources, such as bio-based products, are to be found for making high value base chemicals.

Bio-feedstocks for use in steam crackers need to comply with some technical specifications as the conventional existing steam crackers are designed for hydrocarboneous feedstocks, featured by additional specifications, like boiling point range, metal content and presence of oxygenates. A promising bio-feedstock for steam cracking are fatty acids or triglycerides from various origin like vegetable oils, animal greases, used cooking oils and algae's. They can be produced by autotrophs (in particular photoautotrophs, using sunlight as energy sources to fix CO2 for growth) like plants and algae's or heterotrophs (using reduced carbon for growth; they are photoheterotroph or organotroph when obtaining the needed energy from sunlight or from reduced carbon, respectively) like animals, fungi and many yeasts and bacteria. Most heterotrophic organisms use biogenic material (carbohydrates, proteins and fatty acids) to grow; however, some are able to use hydrocarbon type materials as energy source and for growth, like methanotrophic microorganisms that use methane, either from biogenic or fossil origin. Heterotrophic microorganism and in particular methanotrophic microorganism can naturally or after appropriate genetic modification convert biogenic material or hydrocarbons into fatty acids or derivatives, like triglycerides. The production of such fatty acids and derivates by heterotrophs or autotrophs from CO2, biogenic material or fossil resources is collectively referred to as "biologically produced".

Conventional steam cracker includes a furnace having essentially 2 sections: a convection section and a radiant section. The hydrocarbon feedstock typically enters the convection section of the furnace as a liquid or as vapor for light feedstock's wherein it is heated and/or vaporized by indirect contact with hot flue gas coming from the radiant section and by direct contact with added preheated steam. The vaporized feedstock is then introduced into the radiant section where the cracking takes place to produce light olefins. Conventional steam cracking systems are effective for cracking rather high-quality feedstocks such as ethane, liquefied petroleum gas (LPG), naphtha and to some extend also gasoils. Atmospheric residues, vacuum gasoils and in particular crude oils, contain high molecular weight, non-volatile components with a tail having boiling points in excess of 550° C. Often these tail components are non-volatile and lay down as coke before being vaporized either in the convection section or when entrained also in the radiant section of conventional pyrolysis furnaces. At the point where the lighter components have fully vaporized ("dry point"), only very low levels of non-volatiles can be tolerated. Incipient cracking in the liquid phase must be minimized to avoid fouling of the convection section.

The quality of the heavy gasoil is very important for steam cracking: molecular composition (polyaromatics and heavy naphthenes result in a lot of fuel oil), final boiling point, impacting the ability of vaporization. A typical technical solution to improve the feedstock quality is hydrotreatment of heavy gasoils that can significantly increase the yield of high value chemicals (HVC). Hydrogenation of aromatics, eventually with some ring-opening of naphtenes results in significant less tar make in the benefit of light olefins. Tar make can further be reduced by distilling out the heavy tail of the gasoil.

Heavier feedstocks generally crack easier than the more chemically stable light naphtha, LPG or ethane, but exhibit a higher propensity to form coke. The heat of cracking is also lower for heavier feedstocks so that they reach their maximum light ends yields at lower coil outlet temperature (COT). Maximum severity for any liquid feedstock, meaning maximum light ends yield, is the point of feedstock conversion level where the secondary reactions leading to aromatics formation, in general, and to conjugation of polyaromatics to heavy tars and coke-forming species, begins to increase dramatically. The fast increase in coke-forming moieties beyond this point leads to greatly reduced run length as a result of rapid coke constriction of the coil and quench exchangers. In opposition, lowering the severity noticeably improves run-length, but, however, uncracked liquid feedstock will contribute to the yield of less desired pyrolysis gasoline and pyrolysis fuel oil (PFO).

When heavy hydrocarbons are cracked beyond the point of maximum light ends yield, the formation of polynuclear aromatics increases significantly leading to rapid coking of the coil. In relation to the cracking severity, the cracking residence time needs to be kept short to minimize secondary reactions because many of these secondary reactions are pathways to coke formation. The operating window between maximum light ends yield and controllable coke-make is narrower when the hydrocarbon feedstock becomes heavier.

Typically the heavies (C9+) produced on a steam cracker from naphtha (boiling range 15 to 200° C.) is lower than 6 wt %, whereas for atmospheric gasoil is well above 8 wt % and can amount above 20 wt % for vacuum gasoils. The production of these heavies requires special precautions for coke mitigation and the quench section.

The radiant section effluent of a steam cracker has to be cooled before fractionation of the different cuts can proceed. An indirect or direct quenching is used, where indirect quenching is preferred with respect to energy recovery (production of high pressure steam). In case of heavy liquid hydrocarbons with a high propensity of making tar-like molecules, an indirect quench section can be fouled, resulting in shortening of run length. A tar mist, entrained with the furnace effluent, can stick on tubular exchangers and being still at very high temperature evolves in coke-like deposits. Further down a tubular quench system, heavy fuel oil can condense, resulting in slugging. When a heavy feedstock has a high propensity of making tar-like molecules, a direct quench system where the furnace effluent is cooled with direct contact with a colder stable oil in order to cool and condense the heavy fuel oil as fast as possible is generally proposed.

From the former discussion, it is understood that dependent on the composition and boiling range of the fossil-based feedstock the steam cracker configuration, equipment and optimal operation conditions will be different. When heavy hydrocarbon feedstocks are steam cracked, in order to maximize the light olefins yield while minimizing coke formation and downstream fouling, the steam to hydrocarbon ratio is increased, the total pressure reduced and the coil outlet temperature reduced.

Hence, steam cracking operating conditions may be influenced with the quality or the composition of the feedstock mixture. Steam cracking alternative feedstock mixture, such as biologically produced, may therefore be challenging when operating conditions should remain unchanged.

WO2011/012438 describes the use of fatty acids as feedstock for naphtha steam cracker for the production of light olefins. As the feedstock still contains some oxygen (in the carboxyl moiety), more carbonoxides (CO and $CO_2$) and some short chain water soluble acids are formed. Existing steam crackers are not designed to handle these carbonoxides or lower pH of the aqueous product.

WO2011/012439 discloses a process to convert fatty acids and triglycerides into paraffin's, called bio-naphtha, free from substantial amounts of oxygen and that can be used for steam cracking. These naphtha paraffin's contain 12 to 24 carbons dependent on their origin and hence falling in the boiling range of fossil gasoils. WO2011/012439 discloses that steam cracking n-C15 or n-C20 paraffins instead of fossil naphtha allows the production of greater content in propylene and ethylene. However there is no indication on the impact of such bio-naphtha on the operating conditions of the steam cracker.

CN101723783 discloses a process for the production of ethylene by steam cracking of plant oil or vegetable fat mixed with liquid hydrocarbon oil as a raw material.

WO2014/093016 discloses a process for the production of ethylene from naphtha feedstock comprising a pre-treatment of the naphtha feedstock prior to steam cracking.

US2014/0046103 discloses a process for the production of naphtha from natural occurring triglycerides or fatty acids. The so-produced naphtha can be used as feedstock for hydrocracking or steam cracking. The heavy hydrocarbons are hydrocracked to produce short chain hydrocarbon having from 4 to 10 carbon atoms. The aim of the process is to produce 100% renewable gasoline containing no aromatic hydrocarbons.

WO2014/111598 discloses a process for making a bio-naphtha that can be used in a steam cracker. However there is no teaching of the operating conditions to be used in the steam cracker and no teaching of the impact of the mixing.

EP 2 290 035 discloses similarly a process for the production of a bio naphtha, however this document is silent on the impact of such bio naphtha in a steam cracker unit.

EP 2 290 045 discloses similarly a method of production of a bio naphtha but there is no teaching of the possible impact on the steam cracker unit.

EP 2 917 424 discloses a process for hydrotreating vegetable oils and to crack the products obtained in a steam cracker. However the bio naphtha obtained is cracked only pure and there is no teaching of a possible cracking of a mixture of bio naphtha with usual naphtha.

US 2011/0319683 relates to a general method for producing a naphtha from a renewable feedstock. Again, there is no teaching of the impact of cracking a mixture of a bio naphtha with an usual naphtha.

FR2917424 discloses the treatment of vegetable oils to produce paraffins that are used as a bio-naphtha. However there is no teaching of the impact of this bio-naphtha on the operating conditions of the steam cracker.

There is still a need for processes that allow the production of high value chemicals by steam cracking of biologically produced material without the need for capital intensive modifications or unoptimised operation of conventional naphtha steam crackers.

SUMMARY OF THE INVENTION

In a first aspect, the present invention provides a process for the production of high value chemicals, preferably including at least ethylene, propylene and benzene, and optionally hydrogen, toluene, xylenes and/or 1,3-butadiene. Said process comprises the steps of:
- (a) providing a non-cyclic paraffin stream (A) comprising at least 90 wt % of paraffins having at least 12 carbon atoms,
- (b) providing an hydrocarbon stream (B) comprising at least 90 wt % of components having a boiling point ranging from 15° C. to 200° C. measured with ASTM D86,
- (c) mixing said non-cyclic paraffin stream (A) with said hydrocarbon stream (B) to form a feedstock mixture; the weight content of said non-cyclic paraffin stream (A) in said feedstock mixture is greater than 0.1 wt % preferably greater than 1 wt % more preferably greater than 5 wt % even more preferably greater than 10 wt % the most preferably greater than 20 wt % and preferably lower than 70 wt %, more preferably lower than 60 wt %, the most preferably lower than 50 wt %,
- (d) steam cracking said feedstock mixture with steam in a ratio of 0.2 to 0.5 kg steam per kg of feedstock mixture to obtain cracking products, preferably including at least ethylene, propylene and benzene, and optionally hydrogen, toluene, xylenes and/or 1,3-butadiene;

characterized in that
step (d) is carried out at a steam to hydrocarbon ratio lower than 0.5, and at a coil outlet temperature of at least 820° C. preferably 830° C.

Under the above mentioned operating conditions, the a steam to hydrocarbon ratio stays lower than 110% of such ratio used for steam cracking of only hydrocarbon stream (B) and at a coil outlet temperature stays lower than 102% of such coil outlet temperature used for steam cracking of only hydrocarbon stream (B).

The non cyclic paraffins (i.e. mixture of normal and iso paraffins) having at least 12 carbon atoms have a boiling point in the range of gasoil i.e. a boiling point of at least 210° C. preferably 220° C. measured with ASTM D86. It is generally admitted that a gasoil cannot be steam cracked on a naphtha cracker without modifying at least the operating conditions or the design of the unit. Gasoils have a high final boiling point, and they are not fully vaporized at the outlet of the convection section and droplets of gasoil hitting hot metallic surfaces rapidly lead to fouling and coking of the units. However it has been discovered that due to their particular properties, non cyclic paraffins having a boiling range of a gasoil can be mixed with a conventional naphtha thereby creating an heavier mixture that can be steam cracked in an unit without significantly changing the operating conditions, i.e. that can be steam cracked in an naphtha steam cracker design, employing its typical operating conditions, although it is as heavy as a gasoil.

In other words, it has been discovered that non cyclic paraffins (i.e. mixture of normal and iso paraffins) although having at least 12 carbon atoms have only a small impact on the operating conditions of the steam cracker. Surprisingly the production of high value chemicals is not affected and the coil outlet temperature and the steam to hydrocarbon ratio do not have to be adapted to crack heavier molecules in C12 that are added to the hydrocarbon stream (B). Therefore such non cyclic paraffins can be easily co processed with naphtha, LPG or mixtures of the latter with no major modifications being required to the steam cracker configuration, equipment and operating conditions.

Furthermore, the weight content of ethylene and propylene is increased when the amount of non-cyclic paraffin stream in the feedstock mixture is also increased while maintaining the coil outlet temperature and the steam to hydrocarbon ratio unchanged. Such increase in high value chemicals lowers the formation of undesirable products or coke which finally render the process more efficient.

In addition, the content of non cyclic paraffin can stay as low as 0.1 wt % in said feedstock mixture. In this case, there is only a very small impact on the operating condition but the product obtained can still be attributed a green label thanks to the mass balance concept. Additionally, when it comes to use large plant treating large quantities of naphtha, the availability of non cyclic paraffins may be at stake. This product remains still relatively uncommon, difficult to obtain in large quantities and still expensive. However, it would not depart from the spirit of the invention to have a content of non cyclic paraffin in said feedstock mixture of at least 1 wt %, preferably at least 5 wt %, more preferably 10 wt % the most preferably 20 wt %.

In another embodiment the weight content of linear paraffins originating from said non-cyclic paraffin stream (A) in said feedstock mixture obtained at step (c) is of at most 50 wt % preferably at most 40 wt % more preferably at most 30 wt %. It has been discovered that the content in linear paraffins originating from said non-cyclic paraffin stream (A) should be at a maximum content of 50 wt % otherwise the cloud point of the mixture may be too high. A too elevated cloud point leads to pumpability problems, which can imply significant investments as storage tank may be needed to be heated in order to prevent solidification.

In another embodiment, said non-cyclic paraffin stream (A) is obtained by mixing a stream (a1) comprising at least 90 wt % of linear paraffins with a stream (a2) comprising at least 30 wt %, preferably 50 wt %, most preferably 90 wt % of ramified paraffins. To avoid the problem of a too high cloud point originating from a too high content of linear paraffins, it is preferably possible to partially substitute the linear paraffins with ramified paraffins.

In an advantageous embodiment the ramified paraffins are obtained via the isomerization of the linear paraffins meaning stream (a2) is obtained by isomerizing a part of said stream (a1) preferably in the same reactor.

Advantageously such non cyclic paraffins are produced via hydrodeoxygenation, decarbonylation or decarboxylation from fatty acids and derivates (like mono-, di- and tri-glycerides) or via co processing of such fatty acids and derivates (like mono-, di- and tri-glycerides) with naphtha and/or gasoil including a hydrotreatment of the latter.

In another embodiment, the fatty acids and derivates (like mono-, di- and tri-glycerides) are mixed with a gasoil before being treated in a hydrodesulfurization (HDS) unit. Such co-processing allows obtaining a non cyclic paraffin stream (A) in mixture with a gasoil. It has the interest that an existing HDS unit can be used. Additionally, the gasoil used in such co-processing may contain sulfur and therefore there is no need for additional sulfur compounds to maintain the HDS catalyst under sulfurized state. The mixture hence obtained can be further mixed with said hydrocarbon stream (B) and further steam cracked. In this latter case, the gasoil can be valorized in a existing steam cracker designed to crack naphtha.

In a preferred embodiment, said non-cyclic paraffin stream (A) comprising at least 90 wt % of paraffins having at least 12 carbon atoms is further characterized in that said paraffins having at least 12 carbon atoms comprise at least 30 wt % of linear paraffins or/and less than 20 wt % multiple-branched paraffins, the rest of the composition being single branched paraffins.

In still another embodiment said feedstock mixture obtained at step (c) is further mixed with at least one hydrocarbon stream (B*) prior to step (d) characterized in that said hydrocarbon stream (B*) has an initial boiling point, IBP, of at least 2° C. higher than said hydrocarbon stream (B) and has an final boiling point, FBP, of at least 5° C. higher than said hydrocarbon stream (B). The content of said hydrocarbon stream (B*) is of preferably 5 wt % more preferably 10 wt %, even more preferably 20 wt % in the mixture obtained in step (c). It has been additionally discovered that the mixture to be steam cracked in step (d) can be obtained by mixing said non-cyclic paraffin stream (A) with a naphtha and with an even heavier product without having a significant impact on the operating conditions of the steam cracker unit. In this last case, it is possible to upgrade gasoil that could not be treated alone in the steam cracker with the help of said non-cyclic paraffin stream (A) and thanks to their particular properties.

Furthermore, the present process can be carried out in the presence of either light or heavy naphtha without requiring particular adaptation of the unit. The benefic impact of the non-cyclic paraffins originating from a biological production step counter balances the negative impact of using heavier naphtha or gasoil. In this latter case, a heavier feedstock can be used while adapting the operating conditions to have a constant production of high value chemicals. The present invention thus provides a versatile process suitable for a wide range of feedstocks from usual naphtha to heavier feedstocks like gasoil or mixture thereof as long as they are combined with non cyclic paraffins preferably originating from a biological production step (i.e. preferably produced via hydrodeoxygenation, decarbonylation or decarboxylation from fatty acids and derivates (like mono-, di- and tri-glycerides) or via co processing of such fatty acids and derivates (like mono-, di- and tri-glycerides) with naphtha and/or gasoil including a hydrotreatment of the latter). Such invention presents the additional advantage that it does not require significant changes on the steam cracker unit. The operating conditions and the nature of the feedstock (i.e. the content of non-cyclic paraffins stream (A) with respect to the hydrocarbon stream (B)) are adapted to meet the required production rate of high value chemicals according to procedure known per se by the man skilled in the art.

In a preferred embodiment, the ethylene to methane weight ratio obtained in the cracking products produced at the end of the present process, i.e. step (d), is higher than the ratio obtained for said steam cracking of hydrocarbon stream (B) alone. Such increase is of at least 2% preferably 5% most preferably 10%. The ethylene to methane weight ratio value for steam cracking of said hydrocarbon stream (B) alone is 1.7 or lower. However when the mixture of step (c) is steam cracked according to the invention, the ethylene to methane weight ratio increased as a result of an increase of the yield of ethylene combined with a decrease of the yield of methane. This increased ethylene to methane ratio provides a technical advantage to an often reoccurring technical bottleneck of existing steam crackers which is the extraction of the non-condensable light components (mainly methane and hydrogen) from the low pressure section (furnace) to the high pressure section (fractionation and distillation), requiring cryogenic temperatures combined with compression sections. Therefore lower production rate of methane in a steam cracker allows increasing the overall production of the process as the cold fractionation section and the compressor section are often bottlenecks. The invention is therefore an alternative to increase the overall capacity of the process without requiring investments.

In another aspect, the present invention provides a process for the production of high value chemicals, preferably including at least ethylene, propylene and benzene, and optionally hydrogen, toluene, xylenes and/or 1,3-butadiene, said process comprises the steps of:
(a) providing a non-cyclic paraffin stream (A) comprising at least 90 wt % of components having at least 12 carbon atoms,
(b) providing an hydrocarbon stream (B) comprising hydrocarbons having from 3 to 4 carbon atoms or mixture thereof,
(c) mixing said non-cyclic paraffin stream (A) with said hydrocarbon stream (B) to form a feedstock mixture; preferably the weight content of said non-cyclic paraffin stream (A) in said feedstock mixture is greater than 0.1 wt %; and preferably lower than 70 wt %, more preferably lower than 60 wt %, the most preferably lower than 50 wt %,
(d) steam cracking said feedstock mixture with steam in a ratio of 0.2 to 0.5 kg steam per kg of feedstock mixture to obtain cracking products including at least ethylene, propylene and benzene, and optionally hydrogen, toluene, xylenes and/or 1,3-butadiene;
characterized in that
step (d) is carried out at a steam to hydrocarbon ratio that is lower than 0.5, and at a coil outlet temperature of at least 820° C. preferably 830° C.

Indeed it has been discovered that the non cyclic paraffins can also be mixed with lighter hydrocarbons propane and butane (LPG) and can easily be cracked in a steam cracker without impact on the operating conditions i.e. that the a steam to hydrocarbon ratio stays lower than 110% of such ratio used for steam cracking of only hydrocarbon stream (B) and at a coil outlet temperature stays lower than 102% of such coil outlet temperature used for steam cracking of only hydrocarbon stream (B).

In another aspect, the present invention provides for the production of high value chemicals, preferably including at least ethylene, propylene and benzene, and optionally hydrogen, toluene, xylenes and/or 1,3-butadiene, said process comprises the steps of:
(a) providing a non-cyclic paraffin stream (A) comprising at least 90 wt % of components having at least 12 carbon atoms,
(b) providing an hydrocarbon stream (B) comprising hydrocarbons having from 3 to 4 carbon atoms or mixture thereof and hydrocarbons comprising at least 90 wt % of components having a boiling point ranging from 15° C. to 200° C.,
(c) mixing said non-cyclic paraffin stream (A) with said hydrocarbon stream (B) to form a feedstock mixture; preferably the weight content of said non-cyclic paraffin stream (A) in said feedstock mixture is greater than 0.1 wt % preferably greater than 1 wt % more preferably greater than 5 wt % and preferably lower than 70 wt %, more preferably lower than 60 wt %, the most preferably lower than 50 wt %;
(d) steam cracking said feedstock mixture with steam in a ratio of 0.2 to 0.5 kg steam per kg of feedstock mixture to obtain cracking products including at least ethylene, propylene and benzene, and optionally hydrogen, toluene, xylenes and/or 1,3-butadiene;
characterized in that
step (d) is carried out at a steam to hydrocarbon ratio that is lower than 0, and at a coil outlet temperature of at least 820° C. preferably 830° C.

Under the above mentioned operating conditions, the a steam to hydrocarbon ratio stays lower than 110% of such ratio used for steam cracking of only hydrocarbon stream (B) and at a coil outlet temperature stays lower than 102% of such coil outlet temperature used for steam cracking of only hydrocarbon stream (B).

The other embodiments presented above apply here mutatis mutandis as well as the technical advantages associated.

DEFINITIONS

Figure 1A:
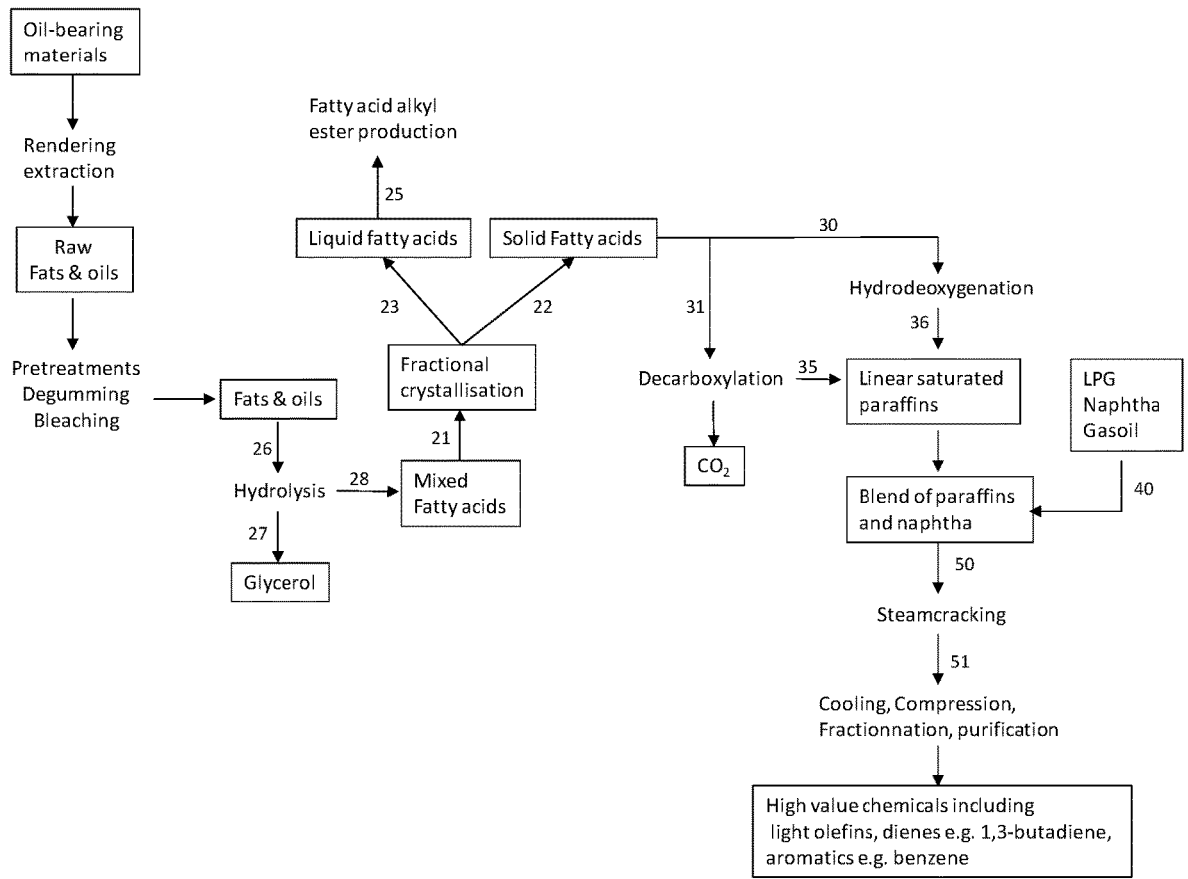
FIGS. 1a-f represent processes according to the present invention wherein the non-cyclic paraffins are prepared according to various embodiments.

Liquefied petroleum gas (LPG) consists essentially of propane and butanes. Petroleum naphtha or naphtha is defined as the hydrocarbons fraction of petroleum having a boiling point from 15° C. up to 200° C. It consists of a complex mixture of linear and branched paraffins (single and multi branched), cyclic paraffins and aromatics having carbons numbers ranging from 5 to about 11 carbons atoms. Light naphtha has a boiling range from 15 to 90° C., consisting of C5 to C6 hydrocarbons while heavy naphtha has a boiling range from 90 to 200° C., consisting of C7 to about C11 hydrocarbons. Gasoils have a boiling range from about 200 to 350° C., consisting of C10 to C22 hydrocarbons, including essentially linear and branched paraffins, cyclic paraffins and aromatics (including mono-, naphtho- and poly-aromatic).

The term "non cyclic paraffins" refers to linear paraffins, single branched paraffins and iso paraffins. It excludes naphthenic and aromatic compounds except at a content of traces or impurities.

Hydrodeoxygenation refers to chemical removal of oxygen atoms from organic molecules by replacing a carbon-oxygen bond by a carbon-hydrogen bond while producing water, e.g.:

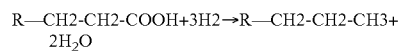
R—CH2-CH2-COOH+3H2→R—CH2-CH2-CH3+ 2H$_2$O

Decarbonylation refers to chemical removal of oxygen atoms from organic molecules by removal the oxygen atom together with carbon as carbonmonoxide, e.g.:

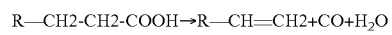
R—CH2-CH2-COOH→R—CH=CH2+CO+H$_2$O

Decarboxylation refers to chemical removal of oxygen atoms from organic molecules by removal the oxygen atom together with carbon as carbondioxide, e.g.:

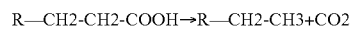
R—CH2-CH2-COOH→R—CH2-CH3+CO2

It shall additionally be understood that the products defined here are rarely completely pure. They are generally obtained via distillation which is not a perfect separation technique. Additionally the characterization techniques have their own limitations and uncertainties. When a reference is made on a product it shall therefore be understood that such product contains at least 98 wt %, preferably 99 wt % most preferably 99.5 wt % of this product the rest of the product being impurities. For instance, a reference to LPG means that it contains at least 98 wt % of propane and butane but it still can contain other products as impurities like traces of ethane and traces of pentane.

DETAILED DESCRIPTION OF THE INVENTION

In a first aspect of the present invention, a process for the production of high value chemicals, preferably at least ethylene, propylene and benzene, and optionally hydrogen, toluene, xylenes and/or 1,3-butadiene, is provided. Said process comprises the steps of:
- (a) providing a non-cyclic paraffin stream (A),
- (b) providing an hydrocarbon stream (B),
- (c) mixing said non-cyclic paraffin stream (A) with said hydrocarbon stream (B) to form a feedstock mixture; the weight content of said non-cyclic paraffin stream (A) in said feedstock mixture is greater than 0.1 wt % and preferably lower than 70 wt %, more preferably lower than 60 wt %, the most preferably lower than 50 wt %,
- (d) steam cracking said feedstock mixture with steam in a ratio of 0.2 to 0.5 preferably 0.2 to 0.6 kg steam per kg of feedstock mixture to obtain cracking products including high value chemicals, preferably at least ethylene, propylene and benzene, and optionally hydrogen, toluene, xylenes and/or 1,3-butadiene;
characterized in that
step (d) is carried out at a steam to hydrocarbon ratio that is lower than 0.6, and at a coil outlet temperature of at least 820° C. preferably 830° C. and Advantageously in step (a) the non-cyclic paraffin stream (A) are produced from fatty acid or mono, di or triglycerides via hydrodeoxygenation, decarbonylation or decarboxylation.

In another embodiment, the process is operated at a coil outlet temperature ranging from 820 to 900° C. at a residence time of 0.01 to 1 seconds.

In a preferred embodiment, the non-cyclic paraffin stream (A) may comprise at least 50 wt % of paraffins having at least 12 carbon atoms, preferably at least 60 wt %, more preferably at least 70 wt %, even more preferably at least 80 wt %, most preferably at least 90 wt %, even most preferably at least 95 wt %, in particular at least 98 wt % of paraffins having at least 12 carbon atoms based on the total amount of said non-cyclic paraffin stream (A).

Preferably, said paraffins contained in said non-cyclic paraffin stream (A) may have from 12 to 25 carbon atoms, preferably from 12 to 20 carbon atoms, more preferably from 14 to 18 carbon atoms, and being present in said stream (A) in the above-mentioned range.

It is preferred that the present invention provides non-cyclic paraffin stream (A) comprising at least 90 wt % of paraffins having at least 12 carbon atoms where the non-cyclic paraffins consist of at least 30 wt % linear paraffins and/or consist of less than 20 wt % multiple-branched paraffins; it is more preferred that it consists of at least 60 wt % linear paraffins and/or less than 15 wt % multiple-branched paraffins and it is even more preferred that is consist of at least 80 wt % linear paraffins and/or less than 10 wt % multiple-branched paraffins and still more preferred that it consists of at least 90 wt % linear paraffins and/or less than 5 wt % multiple-branched paraffins. Multiple-branched paraffin refers to a paraffin that has on its linear paraffin base moiety more than one acyl-branch consisting of one or more carbons.

In a preferred embodiment, the hydrocarbon stream (B) may comprise at least 70 wt %, preferably at least 80 wt %, more preferably at least 90 wt %, most preferably at least 95 wt % of components having a boiling point ranging from 15° C. to 200° C. Alternatively, the hydrocarbon stream (B) may be a stream comprising at least 70 wt %, preferably at least 80 wt %, more preferably at least 90 wt %, most preferably at least 95 wt % of hydrocarbons having from 3 to 4 carbon atoms or mixture thereof.

In a preferred embodiment, the hydrocarbon stream (B*) may comprise at least 70 wt %, preferably at least 80 wt %, more preferably at least 90 wt %, most preferably at least 95 wt % of components having a boiling point ranging from 17° C. to 205° C. Alternatively, the hydrocarbon stream (B*) may be a stream comprising at least 70 wt %, preferably at least 80 wt %, more preferably at least 90 wt %, most preferably at least 95 wt % of hydrocarbons having from 3 to 4 carbon atoms or mixture thereof.

In a preferred embodiment, the cracking products obtained in step (d) of the present process may include one or more of the following products ethylene, propylene, benzene, toluene, xylenes, hydrogen or 1,3-butadiene. Preferably, the cracking products obtained in step (d) of the present process may include as less as possible of methane, pyrolysis fuel oil. In a preferred embodiment the produced ethane is recycled back to the cracking furnace for further steam cracking resulting in essentially more ethylene.

In particular, the cracking products obtained in step (d) of the present process may include ethylene, propylene and benzene, and optionally hydrogen, toluene, xylenes, and 1,3-butadiene. In a preferred embodiment, the ethylene to methane weight ratio obtained in the cracking products is higher than the ratio obtained for steam cracking of hydrocarbon stream (B) comprising at least 90 wt % of components having a boiling point ranging from 15° C. to 200° C. alone. A typical weight ratio value for steam cracking of hydrocarbon stream (B) comprising at least 90 wt % of components having a boiling point ranging from 15° C. to 200° C. is 1.7 or less.

In a preferred embodiment, the feedstock mixture may be mixed with steam in a ratio of 0.25 to 0.45 kg steam per kg of feedstock mixture, more preferably of 0.35 kg steam per kg of feedstock mixture.

In a preferred embodiment, the coil outlet temperature may range from 820 to 875° C., preferably from 820 to 870° C., more preferably from 825 to 860° C., more preferably from 835° C. to 850° C. The coil outlet temperature may influence the content of high value chemicals in the cracking products produced by the present process. For example, the content of benzene in the cracking products resulting from the present process may be increased by operating the steam cracking at coil outlet temperature mentioned above, in particular at coil outlet temperature ranging from 825 to 860° C., more preferably from 830° C. to 850° C.

In a preferred embodiment, the residence time of the feedstock, through the steam cracker, may range from 0.05 to 0.5 seconds, preferably from 0.1 to 0.4 seconds.

In a preferred embodiment, the weight content of said non-cyclic paraffin stream (A) in said feedstock mixture is of at least 0.1 wt %, preferably 1 wt % more preferably 2 wt % even more preferably 3 wt % and most preferably 5 wt % and ranges up to a maximum of 95 wt %, preferably 90 wt %, more preferably 75 wt % even more preferably 60 wt % and most preferably 50 wt % or preferably 25 wt %.

In another embodiment, the hydrocarbon stream (B) comprising at least 90 wt % of components having a boiling point ranging from 15° C. to 200° C. (or naphtha) of step (b) is constituted by a mixture of various hydrocarbon streams having different concentration of hydrocarbons having more than 9 carbon atoms (C9+). Said C9+ content varies from 0.1 wt % to 15 wt %. The C9+ content can for instance be measure according to ASTM D2425. The content of the naphtha having the higher C9+ content is of at least 1 wt %, preferably 5 wt %, more preferably 10 wt %, even more preferably 15 wt %, most preferably 20 wt %, the rest being constituted of the other hydrocarbon stream having a boiling point ranging from 15° C. to 200° C. and a lower C9+ content. In other words, the hydrocarbon stream (B) is composed of a mixture of at least two naphthas having different quality for steam cracking i.e. leading to different HVC yields. It has been indeed discovered that the addition of a non-cyclic paraffin stream (A) allows blending a naphtha of poor quality (containing 10 wt % of C9+ or more) with a naphtha of usual quality (containing a maximum of 5 wt % of C9+ or less) without impacting the operating conditions.

In another embodiment, the non-cyclic paraffin may be obtained from fatty acids or mono-, di- or triglycerides thereof by a thermochemical treatment. The term "thermochemical treatment" may refer to the hydrodeoxygenation, decarbonylation or decarboxylation of fatty acids or mono-, di- or triglycerides thereof. Hence, said non-cyclic paraffin fatty acids having at least 12 carbon atoms may be produced by the hydrodeoxygenation, decarbonylation or decarboxylation of fatty acids, or mono-, di- or triglycerides thereof.

In a particular embodiment, the present process may therefore comprise the steps of:
(a) providing fatty acids, or mono-, di- or triglycerides thereof,
(b) thermochemical treatment said fatty acids, or mono-, di- or triglycerides thereof to form non-cyclic paraffins wherein preferably 90 wt % thereof have at least 12 carbon atoms, said thermochemical treatment comprises the hydrodeoxygenation, decarbonylation or decarboxylation of said fatty acids or mono-, di- or triglycerides thereof.
(c) providing an hydrocarbon stream (B) wherein 90 wt % of its components have a boiling point ranging from 15° C. to 200° C. and mixing thereof with said non-cyclic paraffins obtained in step (b), to form a feedstock mixture, such that the weight content of said non-cyclic paraffins obtained in step (b) in said feedstock mixture is greater than 0.1 wt %, preferably range from 0.1 to 95 wt %, more preferably from 1 to 90 wt %, even more preferably from 2 to 75 wt %, most preferably from 3 to 50 wt %, even most preferably from 5 to 25 wt %,
(d) steam cracking said feedstock mixture with steam in a ratio of 0.25 to 0.5 kg steam per kg of feedstock mixture, preferably in a ratio of 0.35 kg steam per kg of feedstock mixture, to obtain cracking products as defined above; and/or wherein step (d) is carried out at a coil outlet temperature ranging from 810 preferably 820° C. to 875° C., preferably from 820 to 870° C., more preferably from 825 to 860° C., most preferably from 835° C. to 850° C., at a residence time of 0.05 to 0.5 seconds, preferably from 0.1 to 0.4 seconds; at a steam to hydrocarbon ratio lower than 0.6 and/or
the ethylene to methane weight ratio obtained in the cracking products of step (d) is higher than 1.7; and/or
step (d) is carried out at a steam to hydrocarbon ratio that is lower than 110% of such ratio used for steam cracking of only hydrocarbon stream (B), and at a coil outlet temperature that is lower than 102% of such coil outlet temperature used for steam cracking of only hydrocarbon stream (B).

In a preferred embodiment, said thermochemical treated fatty acids or mono-, di- or tri-glycerides thereof may have at least 12 carbon atoms, preferably may have from 12 to 25 carbon atoms, preferably from 12 to 20 carbon atoms, more preferably from 14 to 18 carbon atoms. In a preferred embodiment, at least 50 wt % of the thermochemical treated fatty acids, mono-, di- or tri-glycerides thereof may have at least 12 carbon atoms, preferably at least 60 wt %, more preferably at least 70 wt %, even more preferably at least 80 wt %, most preferably at least 90 wt %, even most preferably at least 95 wt %, in particular at least 98 wt % of the thermochemical treated fatty acids, mono-, di- or tri-glycerides thereof may have at least 12 carbon atoms.

In a preferred embodiment, said thermochemical treatment of fatty acids or mono-, di- or tri-glycerides thereof is carried out in presence of hydrogen in order to hydrogenate at the same time the double bonds, present in the acyl-moiety or produced by the oxygen removal reactions. Hence the final product is paraffinic in nature and the presence of hydrogen allows maintaining a high catalytic activity.

In a preferred embodiment, said fatty acids may be obtained by physical refining, including steam distillation or vacuum distillation, of fats and oils, or said fatty acids are obtained by hydrolysis of triglycerides of fats and oils, or said fatty acids are obtained by acidulation of soaps; preferably said soaps being obtained by saponification of fats and oils or by the chemical refining, including neutralization of free fatty acids, present in the fats and oils, or neutralization of fatty acids obtained from hydrolysis of the fats and oils.

The hydrodeoxygenation, decarbonylation or decarboxylation of fatty acids or mono-, di- or tri-glycerides may be carried out in the presence of hydrogen and of at least one catalyst that can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia or mixtures of the latter or group 10 (Ni, Pt and Pd) and group 11 (Cu and Ag) metals or alloy mixtures supported on high surface area carbon, magnesia, zinc-oxide, spinels ($Mg_2Al_2O_4$, $ZnAl_2O_4$), perovskites ($BaTiO_3$, $ZnTiO_3$), calciumsilicates (like xonotlite), alumina, silica or silica-alumina's or mixtures of the latter.

The hydrodeoxygenation may be carried out at a temperature from 200 to 500° C., under a pressure from 1 MPa to 10 MPa (10 to 100 bars) and with a hydrogen to feedstock ratio from 100 to 2000 Nl/l.

The decarbonylation or decarboxylation may be carried out at a temperature from 100 to 550° C., under a pressure from 0.1 MPa to 10 MPa (1 to 100 bars) and with a hydrogen to feedstock ratio from 0 to 2000 Nl/l.

In a preferred embodiment, said non-cyclic paraffins may be produced (I') by hydrolysis of the fats and oils into glycerol and fatty acids, removal of the glycerol or (I") by physical refining, including a steam distillation or vacuum distillation of fats and oils, or (I''') by acidulation of soaps;

and (II) hydrodeoxygenation, decarbonylation or decarboxylation of the fatty acids, said hydrodeoxygenation, decarbonylation or decarboxylation being conducted in the presence of hydrogen and of at least one catalyst that can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia or mixtures of the latter or group 10 (Ni, Pt and Pd) and group 11 (Cu and Ag) metals or alloy mixtures supported on high surface area carbon, magnesia, zinc-oxide, spinels ($Mg_2Al_2O_4$, $ZnAl_2O_4$), perovskites ($BaTiO_3$, $ZnTiO_3$), calciumsilicates (like xonotlite), alumina, silica or silica-alumina's or mixtures of the latter.

In another preferred embodiment, said non-cyclic paraffins may be produced (I') by hydrolysis of the fats and oils into glycerol and fatty acids, removal of the glycerol or (I") by physical refining, including a steam distillation or vacuum distillation of fats and oils, or (I''') by acidulation of fatty acid soaps, and subsequently (II) decarboxylation of the fatty acids carried out on basic oxides, like alkaline oxides, alkaline earth oxides, lanthanide oxides, zinc-oxide, spinels ($Mg_2Al_2O_4$, $ZnAl_2O_4$), perovskites ($BaTiO_3$, $ZnTiO_3$), calciumsilicates (like xonotlite), either as bulk material or dispersed on neutral or basic carriers, on basic zeolites (like alkali or alkaline earth low silica/alumina zeolites obtained by exchange or impregnation).

In another preferred embodiment, said non-cyclic paraffins may be produced by (I) hydrolysis of the fats and oils into glycerol and fatty acids, removal of the glycerol, and (II) fractionation of fatty acids for obtaining a liquid phase and a solid phase containing fatty acids, and (III) deoxygenation, hydrodeoxygenation, decarbonylation or decarboxylation of the fatty acids, said hydrodeoxygenation, decarbonylation or decarboxylation being conducted in the presence of hydrogen and of at least one catalyst that can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia or mixtures of the latter or group 10 (Ni, Pt and Pd) and group 11 (Cu and Ag) metals or alloy mixtures supported on high surface area carbon, magnesia, zinc-oxide, spinels ($Mg_2Al_2O_4$, $ZnAl_2O_4$), perovskites ($BaTiO_3$, $ZnTiO_3$), calciumsilicates (like xonotlite), alumina, silica or silica-aluminas or mixtures of the latter.

In another preferred embodiment, said non-cyclic paraffins may be produced by (I) hydrolysis of the fats and oils into glycerol and fatty acids, removal of the glycerol and (II) fractionation of fatty acids for obtaining a liquid phase and a solid phase containing fatty acids, (IIIa) neutralization of fatty acids from the solid phase to form soaps and (IIIb) acidulation of soaps to form fatty acids, and subsequently (IV) decarboxylation of the fatty acids which is carried out on basic oxides, like alkaline oxides, alkaline earth oxides, lanthanide oxides, zinc-oxide, spinels ($Mg_2Al_2O_4$, $ZnAl_2O_4$), perovskites ($BaTiO_3$, $ZnTiO_3$), calciumsilicates (like xonotlite), either as bulk material or dispersed on neutral or basic carriers, on basic zeolites (like alkali or alkaline earth low silica/alumina zeolites obtained by exchange or impregnation).

As mentioned above, the hydrocarbon stream (B) may comprise of hydrocarbons having from 3 to 4 carbon atoms or mixture thereof. Hence, the present invention may therefore provide in a second aspect a process for the production of high value chemicals by steam cracking comprising the steps of:

(a) providing a non-cyclic paraffin stream (A) comprising at least 90 wt % of components having at least 12 carbon atoms,
(b) providing an hydrocarbon stream (B) having from 3 to 4 carbon atoms or mixture thereof,
(c) mixing said non-cyclic paraffin stream (A) with said hydrocarbon stream (B) to form a feedstock mixture; preferably the weight content of said non-cyclic paraffin stream (A) in said feedstock mixture is greater than 0.1 wt %,
(d) steam cracking said feedstock mixture with steam in a ratio of 0.25 to 0.5 kg steam per kg of feedstock mixture to obtain cracking products as defined above; wherein step (d) is carried out at a steam to hydrocarbon ratio that is lower than 110% of such ratio used for steam cracking of only hydrocarbon stream (B), and at a coil outlet temperature that is lower than 102% of such coil outlet temperature used for steam cracking of only hydrocarbon stream (B).

In a preferred embodiment, the non cyclic paraffins of step (a) are produced from fatty acid or mono, di or triglycerides via hydrodeoxygenation, decarbonylation or decarboxylation.

In a preferred embodiment, the non-cyclic paraffin stream (A) may comprise at least 50 wt % of components having at least 12 carbon atoms, preferably at least 60 wt %, more preferably at least 70 wt %, even more preferably at least 80 wt %, most preferably at least 90 wt %, even most preferably at least 95 wt %, in particular at least 98 wt % of components having at least 12 carbon atoms based on the total amount of said non-cyclic paraffin stream (A). Preferably, said paraffins contained in said non-cyclic paraffin stream (A) may have from 12 to 25 carbon atoms, preferably from 12 to 20 carbon atoms, more preferably from 14 to 18 carbon atoms, and being present in said stream (A) in the above-mentioned range.

In a preferred embodiment, the cracking products obtained in step (d) of the present process may also include one or more of the following compounds ethylene, propylene, benzene, hydrogen, toluene, xylenes or 1,3-butadiene.

In a preferred embodiment, the ethylene to methane weight ratio obtained in the cracking products is higher than 1.8.

In a preferred embodiment, the feedstock mixture may be mixed with steam, in a ratio of 0.25 to 0.45 kg steam per kg of feedstock mixture, more preferably of 0.35 kg steam per kg of feedstock mixture.

In a preferred embodiment, the coil outlet temperature may range from 810 to 875° C., preferably from 820 to 870° C., more preferably from 825 to 860° C., more preferably from 835° C. to 850° C. The coil outlet temperature may influence the content of high value chemicals in the cracking products produced by the present process. For example, the content of benzene in the cracking products resulting from the present process may be increased by operating the steam cracking at coil outlet temperature mentioned above, in particular at coil outlet temperature ranging from 825 to 860° C., more preferably from 830° C. to 850° C.

In a preferred embodiment, the residence time may range from 0.05 to 0.5 seconds, preferably from 0.1 to 0.4 seconds.

In a preferred embodiment, the weight content of said non-cyclic paraffin stream (A) in said feedstock mixture ranges from 0.1 to 95 wt %, preferably from 1 to 90 wt %, more preferably from 2 to 75 wt %, even more preferably from 3 to 50 wt %, most preferably from 5 to 25 wt %.

In a preferred embodiment, said non-cyclic paraffin may be obtained by the hydrodeoxygenation, decarbonylation or decarboxylation of fatty acids or mono-, di- or triglycerides thereof as detailed above.

Characterization of the Chemical Components

Analysis of the reagents and products are known per se by the man skilled in the art. In particular the boiling point of the products is measured using ASTM D86.

The composition of the various streams is also characterized via ASTM D5443. Additional information is obtained via the well known PIONA analysis. PIONA analysis is a standardized gas-chromatographic technique to determine n-paraffins, i-paraffins, n-olefins, i-olefins, c-olefins, naphthenes, and aromatics (PIONA). For heavier molecules than C10, the content of normal paraffins, iso paraffins and naphtenes is determined using the method UOP990. Full characterization of the mixture shall also be performed via ASTM D2425 and completed with GC×GC or LC-GC×GC according to Journal of Chromatographic Science, Vol. 45, November/December 2007 pages 643-649.

General Procedure of Steam Cracking

Steam crackers are complex industrial facilities that can be divided into three main zones, each of which has several types of equipment with very specific functions: (i) the hot zone including: pyrolysis or cracking furnaces, quench exchanger and quench loop, the columns of the hot separation train (ii) the compression zone including: a cracked gas compressor, purification and separation columns, dryers and (iii) the cold zone including: the cold box, de-methaniser, fractionating columns of the cold separation train, the $C_2$ and $C_3$ converters, the gasoline hydrostabilization reactor. Hydrocarbon cracking is carried out in tubular reactors in direct-fired heaters (furnaces). Various tube sizes and configurations can be used, such as coiled tube, U-tube, or straight tube layouts. Tube diameters range from 1 to 4 inches. Each furnace consists of a convection zone in which the waste heat is recovered and a radiant zone in which pyrolysis takes place. The feedstock mixture is preheated in the convection zone to about 530-650° C. or the feedstock is preheated in the convection section and subsequently mixed with dilution steam before it flows over to the radiant zone, where pyrolysis takes place at coil outlet temperatures varying from 800 to 900° C. and residence times from 0.01 to 1 second as detailed above, depending on the feedstock type and the cracking severity desired. In the case of a naphtha steam cracker the coil outlet temperature is of at least 820° C. with a steam to hydrocarbon ratio of 0.6 whereas in the case of a gasoil the steam to hydrocarbon ratio has to be increased or the temperature has to be decreased to avoid a too rapid coking. As mentioned above, in an advantageous embodiment, the residence time is from 0.05 to 0.5 seconds, preferably from 0.1 to 0.4 seconds. The steam/feedstock mixture weight ratio preferentially ranges from 0.25 to 0.5 kg/kg, preferably from 0.30 to 0.45 kg/kg, more preferably is of 0.35 to 0.4 kg/kg. For steam cracking furnaces, the severity can be modulated by: temperature, residence time and pressure of hydrocarbons. The coil outlet pressure may range from 750 to 950 mbars, preferably from 800 to 900 mbars, more preferably may be approx. 850 mbars. The residence time of the feed in the coil and the temperature are to be considered together. Rate of coke formation will determine maximum acceptable severity. A lower operating pressure results in easier light olefins formation and reduced coke formation. The lowest pressure possible is accomplished by (i) maintaining the output pressure of the coils as close as possible to atmospheric pressure at the suction of the cracked gas compressor (ii) reducing the pressure of the hydrocarbons by dilution with steam (which has a substantial influence on slowing down coke formation). The steam/feedstock ratio may be maintained at a level sufficient to limit coke formation.

Effluent from the pyrolysis furnaces contains unreacted feedstock, desired olefins (mainly ethylene and propylene), hydrogen, methane, a mixture of $C_4$'s (primarily isobutylene and butadiene), pyrolysis gasoline (aromatics in the $C_6$ to $C_8$ range), ethane, propane, di-olefins (acetylene, methyl acetylene, propadiene), and heavier hydrocarbons that boil in the temperature range of fuel oil (pyrolysis fuel oil). This cracked gas is rapidly quenched to 338-510° C. to stop the pyrolysis reactions, minimize consecutive reactions and to recover the sensible heat in the gas by generating high-pressure steam in parallel transfer-line heat exchangers (TLE's). In gaseous feedstock based plants, the TLE-quenched gas stream flows forward to a direct water quench tower, where the gas is cooled further with recirculating cold water. In liquid feedstock based plants, a prefractionator precedes the water quench tower to condense and separate the fuel oil fraction from the cracked gas. In both types of plants, the major portions of the dilution steam and heavy gasoline in the cracked gas are condensed in the water quench tower at 35-40° C. The water-quench gas is subsequently compressed to about 25-35 Bars in 4 or 5 stages. Between compression stages, the condensed water and light gasoline are removed, and the cracked gas is washed with a caustic solution or with a regenerative amine solution, followed by a caustic solution, to remove acid gases ($CO_2$, $H_2S$ and $SO_2$). The compressed cracked gas is dried with a desiccant and cooled with propylene and ethylene refrigerants to cryogenic temperatures for the subsequent product fractionation: front-end demethanization, front-end depropanization or front-end deethanization.

In a front-end demethanization configuration, tail gases (CO, $H_2$, and $CH_4$) are separated from the $C_{2+}$ components first by de-methanization column at about 30 bars. The bottom product flows to the de-ethanization, of which the overhead product is treated in the acetylene hydrogenation unit and further fractionated in the $C_2$ splitting column. The bottom product of the de-ethanization goes to the depropanization, of which the overhead product is treated in the methyl acetylene/propadiene hydrogenation unit and further fractionated in the $C_3$ splitting column. The bottom product of the de-propaniser goes to the de-butanization where the $C_4$'s are separated from the pyrolysis gasoline fraction. In this separation sequence, the $H_2$ required for hydrogenation is externally added to $C_2$ and $C_3$ streams. The required $H_2$ is typically recovered from the tail gas by methanation of the residual CO and eventually further concentrated in a pressure swing adsorption unit. Front-end de-propanization configuration is used typically in steamcracker is based on gaseous feedstock. In this configuration, after removing the acid gases at the end of the third compression stage, the $C_3$ and lighter components are separated from the $C_4$, by de-propanization. The de-propanizer $C_3$- overhead is compressed by a fourth stage to about 30-35 bars. The acetylenes and/or dienes in the $C_3$- cut are catalytically hydrogenated with $H_2$ still present in the stream. Following hydrogenation, the light gas stream is de-methanized, de-ethanized and $C_2$ split. The bottom product of the de-ethanization can eventually be $C_3$ split. In an alternative configuration, the $C_3$- overhead is first de-ethanized and the $C_2$- treated as described above while the $C_3$'s are treated in the $C_3$ acetylene/diene hydrogenation unit and $C_3$ split. The $C_{4+}$ de-propanizer bottom is de-butanized to separate $C_4$'s from pyrolysis gasoline.

There are two versions of the front-end de-ethanization separation sequence. The product separation sequence is identical to the front-end de-methanization and front-end depropanization separation sequence to the third compression stage. The gas is de-ethanized first at about 27 bars to separate $C_2$- components from $C_3$+ components. The overhead $C_2$- stream flows to a catalytic hydrogenation unit, where acetylene in the stream is selectively hydrogenated. The hydrogenated stream is chilled to cryogenic temperatures and de-methanized at low pressure of about 9-10 bars to strip off tail gases. The $C_2$ bottom stream is split to produce an overhead ethylene product and an ethane bottom stream for recycle. In parallel, the $C_3$+ bottom stream from the front-end de-ethanizer undergoes further product separation in a de-propaniser, of which the overhead product is treated in the methyl acetylene/propadiene hydrogenation unit and further fractionated in the $C_3$ splitting column. The bottom product of the de-propaniser goes to the de-butanization where the $C_4$'s are separated from the pyrolysis gasoline fraction. In the more recent version of the front-end de-ethanization separation configuration, the cracked gas is caustic washed after three compression stages, pre-chilled and is then de-ethanized at about 16-18 bars top pressure. The net overhead stream ($C_2$-) is compressed further in the next stage to about 35-37 bars before it passes to a catalytic converter to hydrogenate acetylene, with hydrogen still contained in the stream. Following hydrogenation, the stream is chilled and de-methanized to strip off the tail gases from the $C_2$ bottom stream. The $C_2$'S are split in a low pressure column operating at 9-10 bars pressure, instead of 19-24 bars customarily employed in high pressure $C_2$ splitters that use a propylene refrigerant to condense reflux for the column. For the low-pressure $C_2$ splitter separation scheme, the overhead cooling and compression system is integrated into a heat-pump, open-cycle ethylene refrigeration circuit. The ethylene product becomes a purged stream of the ethylene refrigeration recirculation system.

The ethane bottom product of the $C_2$ splitter is recycled back to steam cracking. Propane may also be re-cracked, depending on its market value. Recycle steam cracking is accomplished in two or more dedicated pyrolysis furnaces to assure that the plant continues operating while one of the recycle furnaces is being decoked.

Many other variations exist of the above-described configurations, in particular in the way the undesired acetylene/dienes are removed from the ethylene and propylene cuts. The steam cracking has no catalyst and thus has nothing to see with the catalytic cracking such as the FCC (Fluid bed Catalytic cracking). In a catalytic cracking the hydrocarbon feedstock is cracked in the presence of a catalyst.

General Procedure for the Thermochemical Treatment of the Fatty Acids or Mono-, Di-, Tri-Glycerides Thereof Said fatty acids or mono-, di-, tri-glycerides thereof may be issued from natural occurring fats and oils or biologically produced fatty acids or its derivatives that can be selected among vegetable oils and animal fats, preferentially inedible highly saturated oils, waste food oils, by-products of the refining of vegetable oils, and mixtures thereof or on-purpose biologically produced fatty acids or mono-, di-, tri-glycerides from either biogenic material, CO2 or fossil hydrocarbons. Said fatty acids or mono-, di-, tri-glycerides thereof may be obtained by physical and/or chemical refining pretreatment of the natural occurring fats and oils or biologically produced fatty acids or its derivatives. Physical refining and alkali/chemical refining differ principally in the way free fatty acids are removed. In chemical refining, free fatty acid, most of the phosphatides, and other impurities are removed during neutralization with an alkaline solution, usually NaOH. In physical refining, the free fatty acid is removed by distillation during deodorization and the phosphatides and other impurities must be removed prior to steam distillation of fats and oils.

Said fatty acids or mono-, di-, tri-glycerides thereof preferably obtained by physical and/or chemical refining pretreatment of the natural occurring fats and oils or biologically produced fatty acids or its derivatives may be thermochemical treated to preferably provide linear saturated paraffins. Various options exist to convert fatty acids or mono-, di-, tri-glycerides thereof into non-cyclic paraffins that can be used as feedstock for the steam cracking in order to produce light olefins, dienes and aromatics:

(i) catalytic hydrodeoxygenation,
(ii) catalytic decarbonylation or decarboxylation, or
(iii) thermal decarboxylation of fatty acids soaps.

The first option consists in hydrodeoxygenation, which removes the oxygen atoms from the fats and oils. This can be done on fatty acids or on mono-, di-, or tri-glycerides thereof. Hydrodeoxygenation may be preferentially carried out in continuous fixed bed reactors, continuous stirred tank reactors or slurry type reactors containing solid catalyst that can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia or mixtures of the latter or group 10 (Ni, Pt and Pd) and group 11 (Cu and Ag) metals or alloy mixtures supported on high surface area carbon, magnesia, zinc-oxide, spinels (Mg2Al2O4, ZnAl2O4), perovskites (BaTiO3, ZnTiO3), calciumsilicates (like xonotlite), alumina, silica or silica-alumina's or mixtures of the latter. It is preferred that the support for the catalytic active phase exhibit low acidity, preferable neutral or basic in order to avoid hydro-isomerisation reactions that would result in branched paraffin's and cracking at elevated temperature and pressure in the presence of hydrogen. Temperature ranges from 200 to 500° C., pressure from 1 MPa to 10 MPa (10 to 100 bars) and hydrogen to fatty acids, or on mono-, di-, or tri-glycerides thereof, feed ratio from 100 to 2000 Nm3/m3 of liquid. For optimum performance and stable continuous operation, it is preferred that the active metal component of the catalyst is in the form of sulfides in case when using Mo and/or Co. Thereto, it is preferred that trace amounts of decomposable sulphur compounds are present or added on purpose to the feedstock in order to keep the metal sulphide in its sulphide state. By way of example, these sulphur compounds can be H2S, COS, CS2, mercaptans (e.g. methylsulfide), thio-ethers (e.g. dimethylsulfide), disulfides (e.g. dimethyldisulfide), thiophenic and tetrahydrothiophenic compounds. Under hydrodeoxygenation conditions several reactions occur. The easiest is the hydrogenation of the double bonds in the alkyl-chain. The more difficult reaction is the removal of oxygen atoms from the C—O bonds. Both the carboxyl-group of the fatty acid as the hydroxyl-group of the glycerol-moiety are hydrodeoxygenated. This results in the production of linear paraffin, resulting from the fatty acid and in propane, resulting from glycerol. Depending on the conditions (catalyst, temperature, hydrogen etc), the carboxyl-group can also be decomposed into CO/CO2 (decarbonylation and decarboxylation) and which on their turn can be even further hydrogenated into methane. The hydrodeoxygenation of fatty acids or on mono-, di-, or tri-glycerides thereof can preferentially also be carried out in presence of naphtha and/or gasoils to do simultaneously hydrotreatment of the latter. The hydrotreatment consist of hydrodesulfurisation, hydrodenitrogenation, hydrodemetallization and hydrodearomatisation. These hydrodeoxygenation and hydrotreatment reactions consume a lot of hydrogen.

The second option consists in decarboxylation or decarbonylation of fatty acids or on mono-, di-, or tri-glycerides. These fatty acids can be obtained from fats and oils by physical refining (including steam/vacuum distillation), by (steam) splitting of triglycerides or by splitting of soaps (acidulation) using acids. Decarbonylation or Decarboxylation may be preferentially carried out in presence of solid catalyst in batch type tank reactors, continuous fixed bed type reactors, continuous stirred tank reactors or slurry type reactors. The catalyst can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia or mixtures of the latter or group 10 (Ni, Pt and Pd) and group 11 (Cu and Ag) metals or alloy mixtures supported on high surface area carbon, magnesia, zinc-oxide, spinels ($Mg_2Al_2O_4$, $ZnAl_2O_4$), perovskites ($BaTiO_3$, $ZnTiO_3$), calciumsilicates (like xonotlite), alumina, silica or silica-alumina's or mixtures of the latter. It is preferred that the support for the catalytic active phase exhibit low acidity, preferable neutral or basic in order to avoid hydro-isomerisation reactions that would result in branched paraffin's and cracking. Decarboxylation can also be carried out on basic oxides, like alkaline oxides, alkaline earth oxides, lanthanide oxides, zinc-oxide, spinels ($Mg_2Al_2O_4$, $ZnAl_2O_4$), perovskites ($BaTiO_3$, $ZnTiO_3$), calciumsilicates (like xonotlite), either as bulk material or dispersed on neutral or basic carriers, on basic zeolites (like alkali or alkaline earth low silica/alumina zeolites obtained by exchange or impregnation).

Although, the decarboxylation reaction does not require hydrogen, it is preferred that the decarboxylation is done in presence of hydrogen that will stabilize the catalytic activity by removing strongly adsorbed unsaturated species (for instance when decarbonylation is the prevalent reaction pathway) from the catalyst surface by hydrogen-addition reactions. The presence of hydrogen can also hydrogenate the double bonds present in the acyl moiety of the fatty acid in order to obtain paraffinic reaction products from the decarbonylation or decarboxylation process. The decarbonylation or decarboxylation of the fatty acids or on mono-, di-, or tri-glycerides can be carried out at 100 to 550° C. in presence of hydrogen at pressures ranging from 0.01 up to 10 MPa. The hydrogen to feedstock ratio is from 0 to 2000 Nl/l. The decarbonylation and decarboxylation of fatty acids or on mono-, di-, or tri-glycerides thereof can preferentially also be carried out in presence of naphtha and/or gasoils to do simultaneously hydrotreatment of the latter. The hydrotreatment consist of hydrodesulfurisation, hydrodenitrogenation, hydrodemetallization and hydrodearomatisation.

When the thermochemical treatment of fatty acids or on mono-, di-, or tri-glycerides is carried out in the presence of hydrogen on catalysts, selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia or mixtures of the latter or group 10 (Ni, Pt and Pd) and group 11 (Cu and Ag) metals or alloy mixtures supported on high surface area carbon, magnesia, zinc-oxide, spinels ($Mg_2Al_2O_4$, $ZnAl_2O_4$), perovskites ($BaTiO_3$, $ZnTiO_3$), calciumsilicates (like xonotlite), alumina, silica or silica-alumina's or mixtures of the latter, the different oxygen-removal reactions, hydrodeoxygenation, decarbonylation and decarboxylation, can occur simultaneously dependent on the catalyst type and operating conditions.

A third option to obtain non-cyclic paraffin is through the thermal decarboxylation of soaps of fatty acids. The soaps can be obtained from the chemical refining of fats and oils by neutralization, producing refined triglycerides and soaps, by neutralization of fatty acids obtained after (steam) splitting of glycerides or by direct saponification of glycerides using basic oxides or basic hydroxides, producing a soap and glycerol. Decarboxylation has been carried out by decomposition of fatty acids in hot compressed water with the aid of alkali-hydroxides, resulting in the production of alkanes and $CO_2$. Calcium-soaps of Tung oil have been reported to decompose by distillation as early as 1947. The preferred soaps are those made of alkaline, alkaline earth, lanthanide, zinc or aluminium cations. The thermal decarboxylation of soap can be carried out by heating until the molten soap starts to decompose into the corresponding paraffin's or olefins and the corresponding metal-carbonate or metal-oxide/hydroxide and $CO_2$. It is preferred that the thermal decomposition of the soaps is carried out in the presence of liquid, supercritical or vaporous water.

Figure 1B:
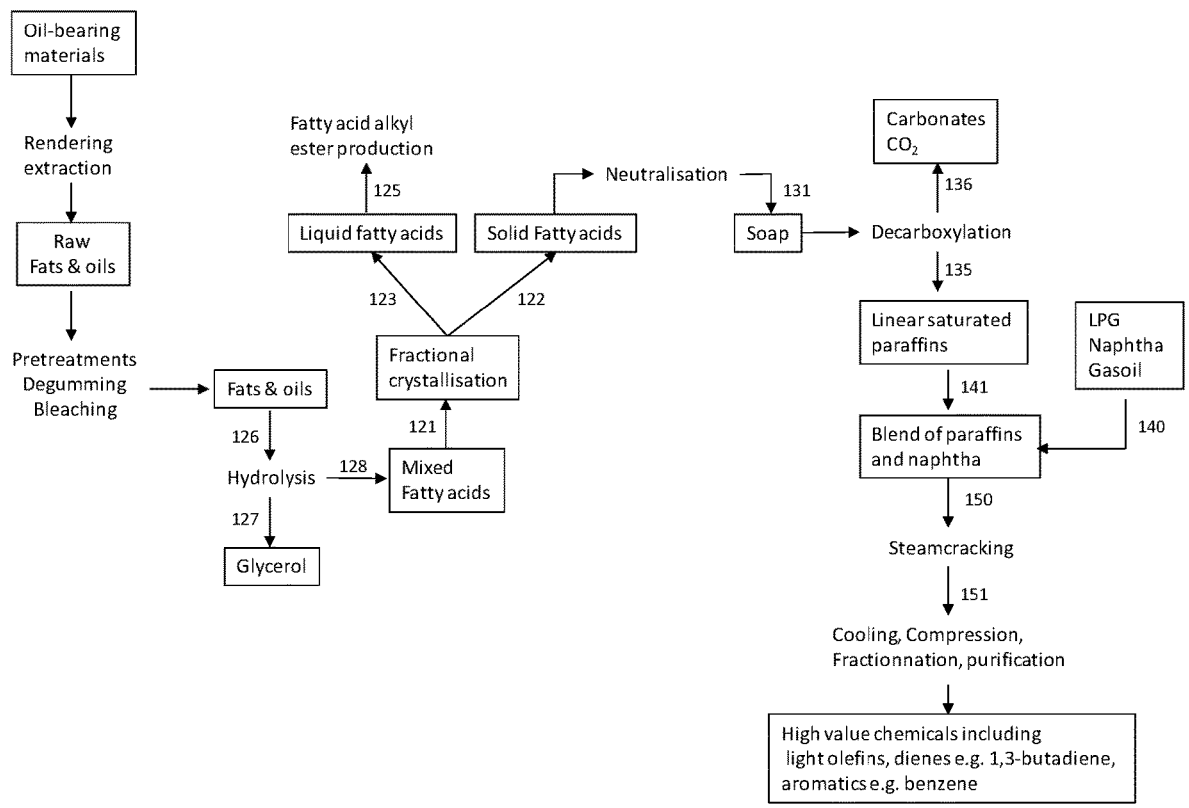

In a particular embodiment of the present invention, non-cyclic paraffin can be obtained from solid fatty acids previously submitted to fractionation treatment. FIGS. 1a-b illustrate such embodiments wherein fatty acids are separated in a liquid fraction and a solid fraction. The fractionation or "dry fractionation" or "dry winterization" is the removal of solids by controlled crystallization and separation techniques involving the use of solvents or dry processing (sometimes also referred to as dewaxing). It relies upon the difference in melting points to separate the oil fractions. The fractionation process has two main stages, the first being the crystallization stage. Crystals grow when the temperature of the molten fat & oil or its solution is lowered, and their solubility at the final or separation temperature determines the fatty acids composition of the crystals formed as well as their mother liquor. Separation process is the second step of fractionation. Several options have been reported, such as vacuum filters, centrifugal separators, conical screen-scroll centrifuges, hydraulic presses, membrane filter presses, or decanters with each their own advantages and drawbacks. Fractionation can occur spontaneously during storage or transport, and this forms the basis of the dry fractionation process. This process is the oldest process type and thanks to steadily improved separation methods it has become competitive on product quality grounds with other, more expensive processes, such as solvent and detergent fractionation. Fractionation can also been carried out in presence of solvents, like paraffins, alkyl-acetates, ethers, ketons, alcohols or chlorinated hydrocarbons. The use of solvents accelerates the crystallization and allows to crystallize more material before the slurry can no more be handled. The term "fractional crystallization" will be used throughout this text and encompasses winterisation, dry fractionation and solvent fractionation.

The solid fatty acids resulting from the fractionation treatment can be converted into non-cyclic paraffins by hydrodeoxygenation, decarbonylation or catalytic decarboxylation (FIG. 1a) or by thermal decarboxylation of soaps of fatty acids (FIG. 1b). Hydrodeoxygenation, decarbonylation, decarboxylation and thermal decarboxylation are disclosed above.

FIG. 1a illustrates a particular embodiment of the process according to the present invention wherein fractionation is carried out. Fats and oils 26 are hydrolyzed to recover mixed fatty acids 28 and glycerol 27. The mixed free fatty acids 28 are fractional crystallized 21, resulting in a solid phase 22 and a liquid phase 23 fractions. The solid phase 22 can be sent to a hydrodeoxygenation section 30 or to a decarbonylation/decarboxylation section 31 where they are converted into non-cyclic paraffins 35, 36. These non-cyclic paraffins are blended with fossil LPG, naphtha or gasoil 40 and hence the blend is steam cracked 50. The products of the steam cracking are cooled, compressed, fractionated and purified 51. The liquid phase 23, obtained from the fractional crystallization is sent to biodiesel production section 25.

In another embodiment (FIG. 1b), fats and oils 126 are hydrolyzed to recover mixed fatty acids 128 and glycerol 127. The mixed free fatty acids 128 are fractional crystallized 121, resulting in a solid phase 122 and a liquid phase 123 fractions. The free fatty acids of the solid phase 122 are neutralized to produce soaps 131. The soaps can be sent to the decarboxylation section where they are converted into non-cyclic paraffins 135 and metal-carbonates or $CO_2$ 136. The non-cyclic paraffins 141 are blended with fossil LPG, naphtha or gasoil 140 and hence the blend is steam cracked 150. The liquid phase 123, obtained from the fractional crystallization is sent to biodiesel production section 125.

Figure 1C:
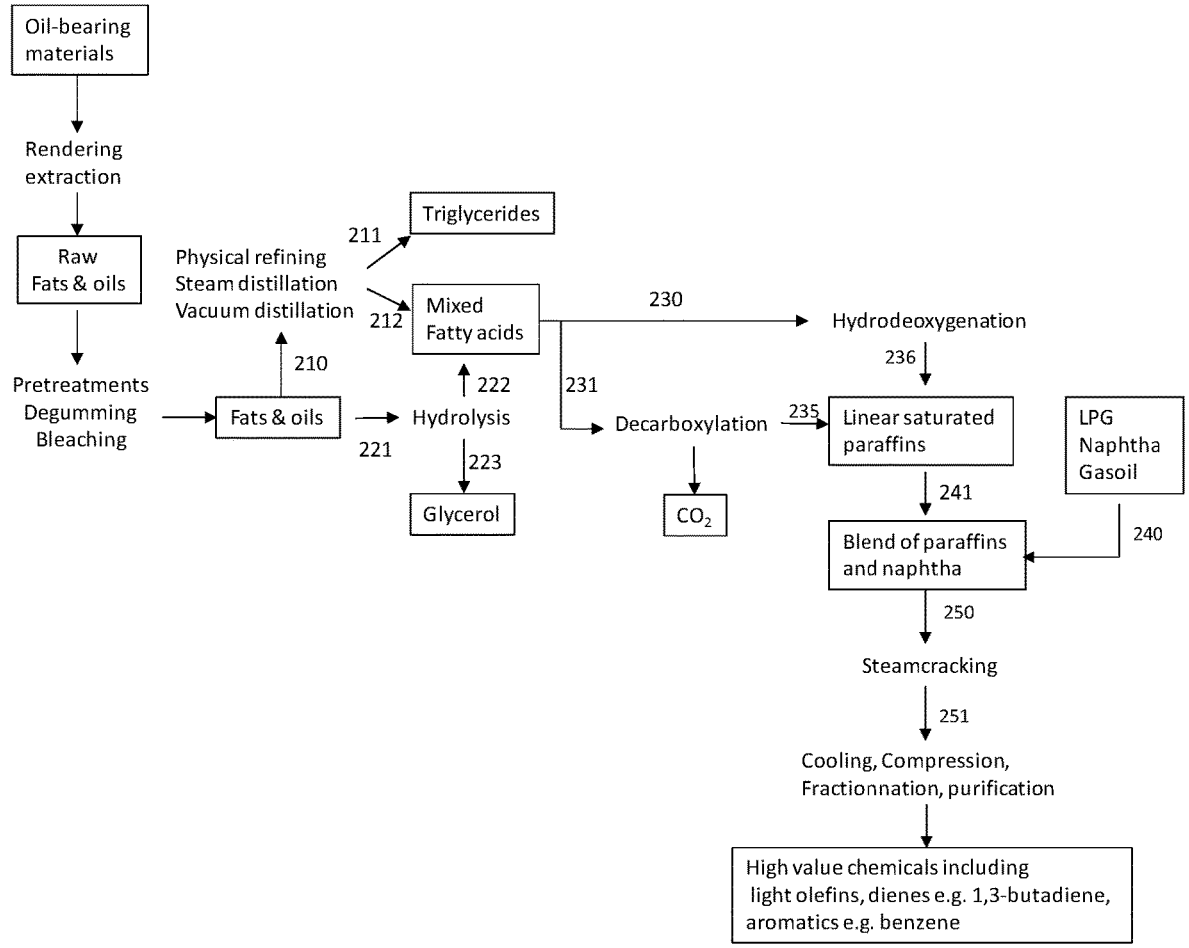

In an embodiment represented in FIG. 1c, fats and oils are physically refined by vacuum distillation or steam distillation 210 to recover the mixed fatty acids 212 as overhead product and the triglycerides 211 as bottom product. Optionally fats & Oils can be hydrolyzed 221 to produce mixed fatty acids 222 and glycerol 223. The quality of the mixed fatty acids can be further improved by hydrogenation of double bonds in the acyl-moiety or before hydrolysis; the fats and oils can be hydrogenated to remove the remaining double bonds and subsequently sent 221 to the hydrolysis step. The mixed fatty acids can be sent 230 to a hydrodeoxygenation section where they are converted into non-cyclic paraffins 236 or alternatively they can be sent to the decarbonylation/decarboxylation section 231 where they are converted into non-cyclic paraffins 235. The non-cyclic paraffins 241 are blended with fossil LPG, naphtha or gasoil 240 and steamcracked 250. The products of the steam cracking are cooled, compressed, fractionated and purified 251.

Figure 1D:
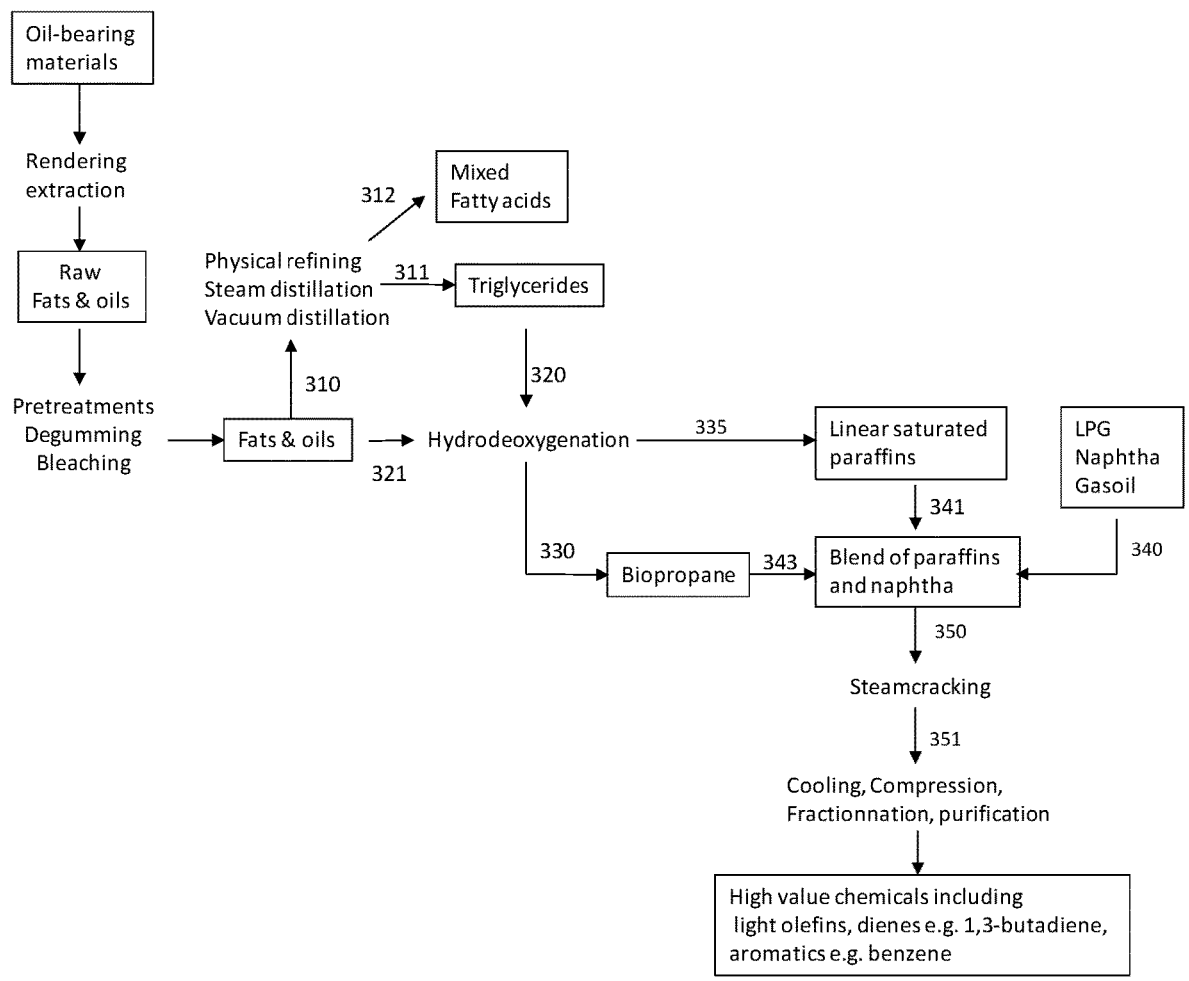

FIG. 1d represents a process according to a particular embodiment of the present invention wherein Fats & Oils are physically refined by vacuum distillation or steam distillation 310 to recover the mixed fatty acids 312 as overhead product and the triglycerides 311 as bottom product. Either the fats & oils, eventually still containing free fatty acids 321 or the physically refined triglycerides 320 acids can be sent to a hydrodeoxygenation section where they are converted into non-cyclic paraffins 335 and bio-propane 330. The non-cyclic paraffins 341 and bio-propane 343 are blended with fossil LPG, naphtha or gasoil 340 and sent to the steamcracker 350. The products of the steam cracking are cooled, compressed, fractionated and purified 351.

Figure 1E:
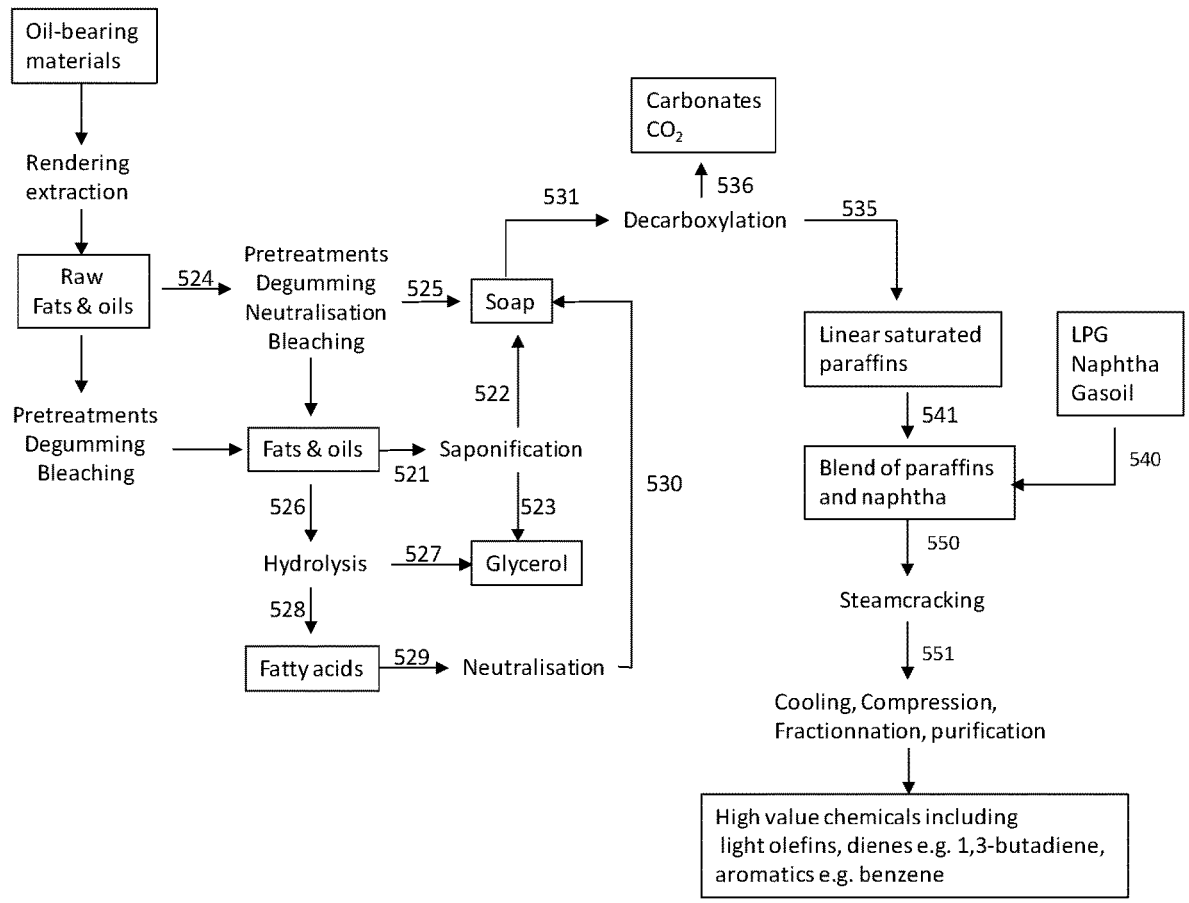

In another embodiment (FIG. 1e), fats and oils are saponificated 521 to recover the soap 522 and glycerol 523. Optionally fats and oils can be hydrolyzed to produce mixed fatty acids and glycerol. Alternatively, soap 525 can be obtained during a chemical refining step of raw fats and oils 524 by the neutralization step. Still another source of soap 530 is via neutralization 529 of fatty acids, obtained by (steam) splitting 526 of fats & oils, producing fatty acids 528 and glycerol 527. The fats and oils are hydrogenated to remove the remaining double bonds and subsequently sent to the saponification 521 or hydrolysis 526 step. The soaps can be sent 531 to the decarboxylation section where they are converted into non-cyclic paraffins 535 and metal-carbonates or $CO_2$ 536. The non-cyclic paraffins 541 are blended with fossil LPG, naphtha or gasoil 540 and steam-cracked 550. The products of the steam cracking are cooled, compressed, fractionated and purified 551.

Figure 1F:
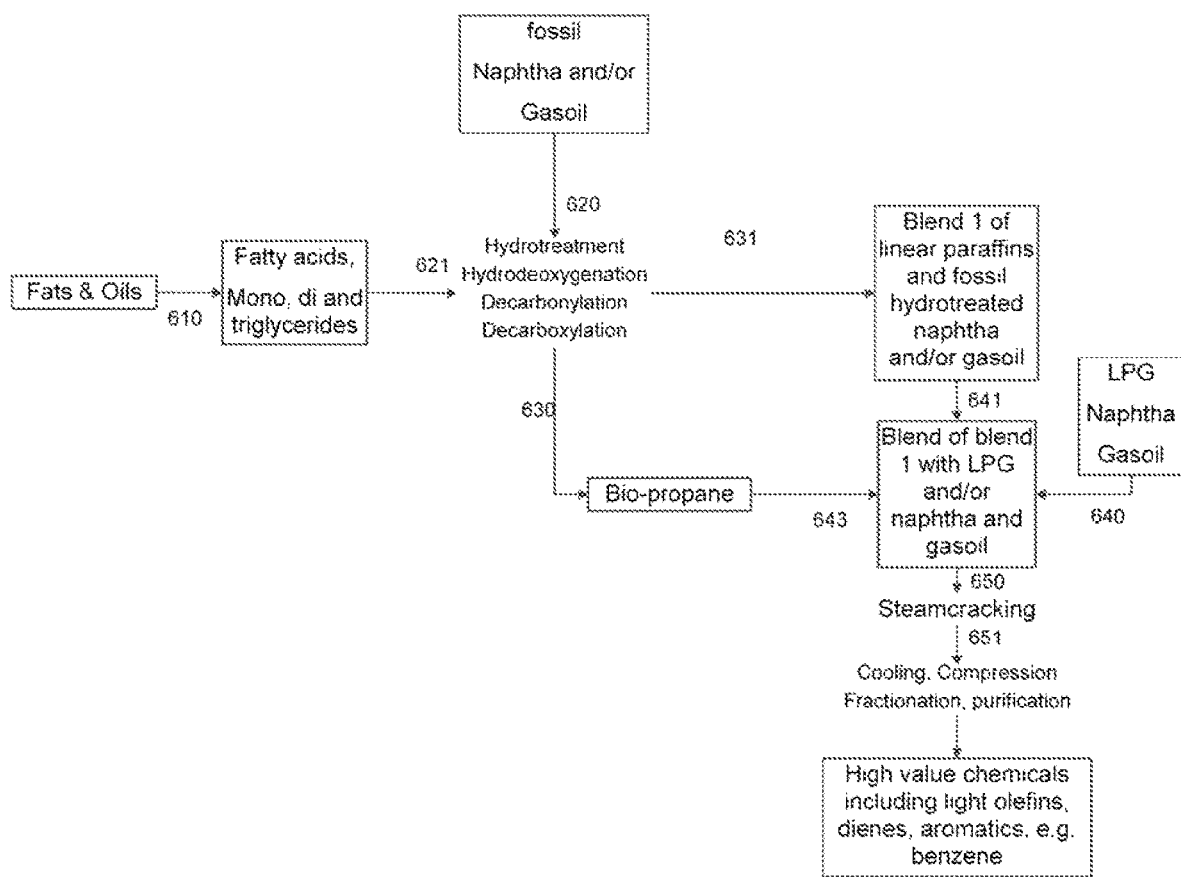

FIG. 1f represents a process according to a particular embodiment of the present invention wherein Fats & Oils are physically and/or chemical refined (see former figures) to recover the mixed fatty acids, mono, di or triglycerides 610 as product. These fatty acids, mono, di or triglycerides and any mixtures of the latter can be sent 621 together with fossil naphtha and/or gasoils fractions 620 to a common thermochemical treatment section that performs hydrotreatment, hydrodeoxygenation, decarbonylation and/or decarboxylation where they are converted into substantially non-cyclic paraffins 631 and bio-propane 630. The fossil naphtha and/or gasoils fractions are simultaneously hydrotreated, including hydrodesulfurisation, hydrodenitrogenation, hydrodearomatisation and/or hydrodemetalisation. The blend of substantially non-cyclic paraffins with hydrotreated fossil naphtha and/or gasoil 641 and eventually bio-propane 643 are blended with fossil LPG, naphtha or gasoil 640 and sent to the steamcracker 650. The products of the steam cracking are cooled, compressed, fractionated and purified 651.

The cracking products obtained according to processes represent in FIGS. 1a-1f or any combination of them comprise light olefins (ethylene, propylene and butenes), dienes (butadiene, isoprene, (di) cyclopentadiene and piperylenes), aromatics (benzene, toluene and mixed xylenes) as main components. Methane, ethane and propane can also be obtained.

EXAMPLES

Example 1—SPYRO Simulation

The steam cracking of naphtha, linear saturated paraffins, saturated isoparaffins, i.e. branched saturated paraffins, and mixtures of naphtha and non-cyclic paraffins was evaluated by SPYRO software to simulate the product distribution. Reference naphtha was also considered: the PIONA analysis of this naphtha here after named naphtha 1 is given in table 1. The operating conditions and the products resulting from steam cracking of naphtha 1 pure, n C15 pure and iso C15 and the various mixture of naphtha 1 and n C15 are detailed in table 2 below. iso C15 refers to a mixture of multi-branched non-cyclic paraffins having 15 carbons. It can be seen from table 2, according to SPYRO simulation, that the steam cracking of non-cyclic linear paraffins (n C15) produce greater content of ethylene than naphtha or steam cracked multiple-branched iso-paraffins. In addition the sum of all high value chemicals (ethylene, propylene, butadiene, benzene and hydrogen) is significantly higher for the linear paraffins. Such linear paraffins produce much less methane and C9+ components. The mixture of naphtha and non-cyclic linear paraffins provides, according to SPYRO simulation, higher content of ethylene and propylene compared with naphtha 1 alone. The HVC yield and ultimate HVC (after recycling of ethane to the furnace, assuming 80% yield to ethylene) is in all blends higher than naphtha 1 only. The ethylene/methane ratio is for all blends higher than for naphtha, being here 1.7. Furthermore, the blends do not result in higher C9+ components. The heat duty for the radiation section par unit HVC is lower for the blends with linear paraffins, having more than 12 carbons.

TABLE 1

PIONA analysis of naphtha 1

| NAPHTHA | N paraffins | Iso paraffins | N olefins | Iso olefins | Cyclo olefins | naphthenic | aromatics | TOTAL |
|---|---|---|---|---|---|---|---|---|
| 4 | 2.26 | 0.25 | 0.18 | 0.06 | 0.00 | 0.00 | 0.00 | 2.75 |
| 5 | 14.75 | 10.61 | 1.05 | 2.13 | 0.49 | 3.42 | 0.00 | 32.45 |
| 6 | 12.85 | 15.69 | 0.06 | 0.17 | 0.02 | 7.81 | 3.12 | 39.72 |
| 7 | 3.49 | 6.93 | 0.00 | 0.00 | 0.00 | 5.21 | 1.45 | 17.08 |
| 8 | 1.02 | 1.43 | 0.00 | 0.00 | 0.00 | 1.47 | 0.84 | 4.76 |
| 9 | 0.65 | 0.89 | 0.00 | 0.00 | 0.00 | 0.61 | 0.34 | 2.49 |
| 10 | 0.16 | 0.47 | 0.00 | 0.00 | 0.00 | 0.00 | 0.05 | 0.68 |
| 11 | 0.03 | 0.06 | 0.00 | 0.00 | 0.00 | 0.00 | 0.00 | 0.09 |
| TOTAL | 35.21 | 36.33 | 1.29 | 2.36 | 0.51 | 18.52 | 5.80 | 100.02 |

| | | |
|---|---|---|
| D86: Distillation ASTM D86 T° C. @ IBP | 33.1 | °C. |
| D86: T° C. @ 50% vol | 63.0 | °C. |
| D86: T° C. @ FBP | 152.2 | °C. |
| Density @ 15° C. | 0.6826 | g/ml |

TABLE 2

SPYRO simulation of reference Naphtha 1, n-C15 and iso-C15 and of mixture of naphtha 1 and n-C15

| | | NAPHTHA 1 | n-C15 | iso-C15 | NAPHTHA 1 + n-C15 (wt/wt) 50/50 | 70/30 | 80/20 | 90/10 |
|---|---|---|---|---|---|---|---|---|
| OPERATING CONDITIONS | | | | | | | | |
| Residence time | s | 0.362 | 0.393 | 0.396 | 0.377 | 0.371 | 0.368 | 0.365 |
| STEAM TO OIL RATIO | KG/KG | 0.30 | 0.30 | 0.30 | 0.30 | 0.30 | 0.30 | 0.30 |
| Coil outlet pressure | BARA | 1.60 | 1.60 | 1.60 | 1.60 | 1.60 | 1.60 | 1.60 |
| Coil outlet temperature | °C. | 820 | 820 | 820 | 820 | 820 | 820 | 820 |
| PRODUCT YIELDS | | | | | | | | |
| CO | WT % | 0.05 | 0.05 | 0.05 | 0.05 | 0.05 | 0.05 | 0.05 |
| CO2 | | 0.00 | 0.00 | 0.00 | 0.00 | 0.00 | 0.00 | 0.00 |
| HYDROGEN | | 0.87 | 0.63 | 0.67 | 0.73 | 0.78 | 0.81 | 0.83 |
| METHANE | | 15.52 | 11.30 | 14.27 | 13.21 | 14.09 | 14.55 | 15.03 |
| ACETYLENE | | 0.28 | 0.31 | 0.32 | 0.28 | 0.28 | 0.28 | 0.28 |
| ETHYLENE | | 26.44 | 36.35 | 28.33 | 31.42 | 29.44 | 28.45 | 27.45 |
| ETHANE | | 4.04 | 6.04 | 4.76 | 5.05 | 4.65 | 4.44 | 4.24 |
| MAPD | | 0.58 | 0.43 | 0.68 | 0.49 | 0.52 | 0.54 | 0.56 |
| PROPYLENE | | 15.87 | 17.08 | 16.29 | 16.60 | 16.32 | 16.17 | 16.02 |
| PROPANE | | 0.48 | 0.68 | 0.70 | 0.57 | 0.53 | 0.52 | 0.50 |
| 1,3-BUTADIENE | | 4.55 | 6.67 | 5.58 | 5.51 | 5.10 | 4.90 | 4.72 |
| 1-BUTENE | | 1.45 | 1.83 | 1.45 | 1.65 | 1.56 | 1.52 | 1.48 |
| ISOBUTENE | | 2.87 | 0.19 | 2.84 | 1.55 | 2.09 | 2.35 | 2.61 |
| 2-BUTENE | | 0.90 | 0.74 | 0.79 | 0.86 | 0.89 | 0.90 | 0.90 |
| ISOBUTANE | | 0.07 | 0.02 | 0.04 | 0.05 | 0.06 | 0.06 | 0.07 |
| NBUTANE | | 0.36 | 0.08 | 0.05 | 0.24 | 0.29 | 0.32 | 0.34 |
| OTHER C4 | | 0.04 | 0.06 | 0.05 | 0.05 | 0.05 | 0.04 | 0.04 |
| C5 CUT | | 4.94 | 3.63 | 4.00 | 4.51 | 4.74 | 4.82 | 4.88 |
| C6 NONARO | | 1.74 | 0.56 | 1.07 | 1.34 | 1.55 | 1.62 | 1.69 |
| BENZENE | | 8.43 | 7.23 | 8.75 | 7.60 | 7.89 | 8.05 | 8.24 |
| C7 NONARO | | 0.41 | 0.18 | 0.31 | 0.35 | 0.39 | 0.40 | 0.41 |
| TOLUENE | | 3.39 | 2.01 | 3.48 | 2.65 | 2.94 | 3.09 | 3.24 |
| C8 NONARO | | 0.04 | 0.03 | 0.03 | 0.04 | 0.04 | 0.04 | 0.04 |
| ETHYLBENZENE/XYLENES | | 0.88 | 0.30 | 0.81 | 0.60 | 0.72 | 0.77 | 0.83 |
| STYRENE | | 0.92 | 0.71 | 0.81 | 0.81 | 0.86 | 0.88 | 0.90 |
| C9+ | | 4.88 | 2.91 | 3.86 | 3.79 | 4.20 | 4.42 | 4.65 |
| HVC | wt % | 56.16 | 67.95 | 59.62 | 61.86 | 59.52 | 58.38 | 57.26 |
| Ultimate HVC | wt % | 59.39 | 72.79 | 63.43 | 65.90 | 63.23 | 61.94 | 60.65 |
| Ethylene/methane ratio | wt %/wt % | 1.70 | 3.22 | 1.98 | 2.38 | 2.09 | 1.96 | 1.83 |
| DUTY RADIATION/HVC | wt % | 0.473 | 0.459 | 0.488 | 0.463 | 0.467 | 0.469 | 0.471 |

\* n-paraffins C15 refers to linear non-cyclic paraffins having 15 carbon atoms here explicitly to pentadecane; iso-paraffins C15 refers to multiple-branched saturated paraffins having 15 carbon atoms

Examples 2 and 3

Tests on a pilot steam cracker were performed with various feedstock mixtures: naphtha only, and a 50/50 weight mixture of naphtha and thermochemical treated palm oil or jatropha oil. The raw palm oil and jatropha oil used during this testing has the composition given in table 3:

TABLE 3

Typical palm oil and *jatropha* oil composition (wt %)

| Compounds | Palm oil | *Jatropha* oil |
|---|---|---|
| C14:0 | 1.0 | 1.6 |
| C16:0 | 44.3 | 7.9 |
| C16:1 | 0.4 | 0.4 |
| C18:0 | 4.6 | 3.7 |
| C18:1 | 38.7 | 62.6 |
| C18:2 | 10.5 | 19.9 |
| C18:3 | 0.0 | 0.1 |
| C20:0 | 0.0 | 0.3 |
| C20:1 | 0.0 | 0.3 |
| Unknown | 0.9 | 3.2 |

The hydrodeoxygenation of palm oil was performed with a pre-sulfided commercial CoMo catalyst at a liquid hourly space velocity of 1.5 h-1, at a temperature about 338° C., under a pressure of 4 MPa and with hydrogen to palm oil ratio of 1500 Nl/l. The hydrodeoxygenated palm oil obtained was mainly composed with n-C14 to n-C18 and contained still about 100-600 wppm of oxygen.

The hydrodeoxygenation of jatropha oil, doped with 1000 wppm of sulfur (as DMDS) was carried out over a pre-sulfided commercial NiMo catalyst at a liquid hourly space velocity of 1.85 h-1, at a temperature of 300 to 360° C., under a pressure of 6 MPa and with hydrogen to jatropha oil ratio of 1050 Nl/l. The remaining oxygen in the product was always below 300 wppm and contained essentially C15 to C18 linear paraffins.

Steam cracking was performed at 850 mbars pressure, a water/hydrocarbon weight ratio of 0.4 and a residence time of about 0.25 seconds. Example 2 is according to the present invention and relates to the steam cracking of a 50/50 weight mixture of naphtha and thermochemically treated palm oil. Example 3 relates to the steam cracking of thermochemically treated jatropha oil blended with typical naphtha (naphtha 3) in a weight ratio of 30/70. The PIONA analysis of naphtha 3 is given in table 3.

TABLE 3

PIONA analysis of naphtha 3

| NAPHTHA | N paraffins | Iso paraffins | N olefins | Iso olefins | Cyclo olefins | naphthenic | aromatics | TOTAL |
|---|---|---|---|---|---|---|---|---|
| 4 | 1.84 | 0.11 | 0.00 | 0.00 | 0.00 | 0.00 | 0.00 | 1.96 |
| 5 | 17.47 | 13.57 | 0.07 | 0.14 | 0.00 | 1.51 | 0.00 | 32.77 |
| 6 | 16.33 | 19.88 | 0.01 | 0.08 | 0.00 | 8.21 | 2.36 | 46.87 |
| 7 | 3.46 | 8.82 | 0.00 | 0.00 | 0.00 | 4.35 | 1.04 | 17.67 |
| 8 | 0.04 | 0.37 | 0.00 | 0.00 | 0.00 | 0.29 | 0.00 | 0.70 |
| 9 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 |
| TOTAL | 39.15 | 42.75 | 0.09 | 0.23 | 0.00 | 14.36 | 3.40 | 99.97 |

The examples 2 and 3 in table 4 show that the amount of ethylene, 1,3 butadiene or ethane was increased while the amount of methane was decreased when a mixture of substantially non-cyclic paraffin and naphtha was steam cracked instead of naphtha alone. The total yield of HVC and ultimate HVC are significantly improved while the ethylene/methane ratio is always higher than the ratio obtained with only fossil naphtha.

TABLE 4

Operating conditions and analysis of the effluents for the steam cracking according to examples 2 and 3.

|  |  | Naphtha 3 | Thermo-chemically treated palm oil | blend 50/50 (*) | Naphtha 3 | Thermo-chemically treated jatropha oil | Blend 70/30 (**) |
|---|---|---|---|---|---|---|---|
| OPERATING CONDITIONS |  |  |  |  |  |  |  |
| Residence time | s | 0.25 | 0.25 | 0.25 | 0.25 | 0.25 | 0.25 |
| STEAM TO OIL RATIO | KG/KG | 0.4 | 0.4 | 0.4 | 0.4 | 0.4 | 0.4 |
| Coil outlet pressure | BARA | 1.85 | 1.85 | 1.85 | 1.85 | 1.85 | 1.85 |
| Coil outlet temperature | ° C. | 847 | 847 | 847 | 847 | 847 | 847 |
| PRODUCT YIELDS |  |  |  |  |  |  |  |
| CO | WT % | 0.05 | 0.11 | 0.07 | 0.05 | 0.07 | 0.04 |
| CO2 |  | 0.03 | 0.10 | 0.07 | 0.00 | 0.00 | 0.04 |
| HYDROGEN |  | 0.91 | 0.60 | 0.75 | 0.89 | 0.58 | 0.79 |
| METHANE |  | 16.05 | 12.19 | 14.30 | 15.89 | 12.04 | 15.01 |

TABLE 4-continued

Operating conditions and analysis of the effluents for the steam cracking according to examples 2 and 3.

|  |  | Naphtha 3 | Thermo-chemically treated palm oil | blend 50/50 (*) | Naphtha 3 | Thermo-chemically treated jatropha oil | Blend 70/30 (**) |
|---|---|---|---|---|---|---|---|
| ACETYLENE |  | 0.45 | 0.50 | 0.49 | 0.43 | 0.45 | 0.45 |
| ETHYLENE |  | 28.06 | 36.74 | 33.00 | 27.18 | 35.89 | 29.81 |
| ETHANE |  | 4.09 | 4.59 | 4.40 | 4.41 | 4.70 | 4.73 |
| MAPD |  | 0.85 | 0.46 | 0.67 | 0.82 | 0.45 | 0.73 |
| PROPYLENE |  | 16.73 | 14.98 | 15.70 | 17.13 | 15.00 | 16.99 |
| PROPANE |  | 0.51 | 0.47 | 0.48 | 0.56 | 0.55 | 0.58 |
| 1,3-BUTADIENE |  | 4.57 | 5.88 | 5.16 | 4.50 | 5.80 | 4.87 |
| 1-BUTENE |  | 1.37 | 0.82 | 1.05 | 1.52 | 0.84 | 1.43 |
| ISOBUTENE |  | 3.07 | 0.18 | 1.52 | 3.26 | 0.21 | 2.46 |
| 2-BUTENE |  | 0.96 | 0.62 | 0.77 | 1.07 | 0.64 | 0.98 |
| ISOBUTANE |  | 0.05 | 0.01 | 0.02 | 0.05 | 0.01 | 0.04 |
| NBUTANE |  | 0.14 | 0.00 | 0.03 | 0.20 | 0.07 | 0.14 |
| OTHER C4 |  | 0.18 | 0.14 | 0.18 | 0.17 | 0.05 | 0.17 |
| C5 CUT |  | 5.62 | 4.12 | 4.54 | 6.16 | 4.16 | 5.57 |
| C6 NONARO |  | 2.21 | 1.11 | 1.56 | 2.54 | 1.18 | 2.14 |
| BENZENE |  | 7.37 | 8.05 | 7.68 | 6.92 | 8.22 | 6.81 |
| C7 NONARO |  | 0.41 | 0.22 | 0.30 | 0.46 | 0.26 | 0.38 |
| TOLUENE |  | 2.34 | 2.14 | 2.24 | 2.22 | 2.30 | 2.03 |
| C8 NONARO |  | 0.10 | 0.09 | 0.09 | 0.11 | 0.11 | 0.10 |
| ETHYLBENZENE/XYLENES |  | 0.44 | 0.40 | 0.43 | 0.41 | 0.45 | 0.38 |
| STYRENE |  | 0.79 | 1.12 | 0.98 | 0.70 | 1.25 | 0.73 |
| C9+ |  | 2.65 | 4.34 | 3.53 | 2.36 | 4.68 | 2.59 |
| HVC |  | 57.65 | 66.26 | 62.29 | 56.61 | 65.49 | 59.26 |
| Ultimate HVC |  | 60.93 | 69.93 | 65.81 | 60.14 | 69.25 | 63.05 |
| Ethylene/methane ratio | wt/wt | 1.75 | 3.01 | 2.31 | 1.71 | 2.98 | 1.99 |

(*) blend 50/50 refers to a blend of 50 wt % of naphtha 3 with 50 wt % of thermochemically treated palm oil.
(**) Blend 70/30 refers to a blend of 70 wt % of naphtha 3 with 30 wt % of thermochemically treated jatropha oil.

Example 4

This example demonstrates that the addition of non cyclic paraffins to a given naphtha quality, like naphtha 1 (see table 1 for composition), unexpectedly, room is created to add a naphtha of lower quality, like naphtha 2 (see table 5 for composition) or even a heavier gasoil fraction, i.e. a larger amount of HVC can be produced when such naphtha's are steam cracked. In other words, while maintaining the operating conditions constant and the HVC production constant, the addition of non cyclic paraffins allows valorizing poorer quality naphtha in combination with other naphtha of higher quality.

TABLE 5

PIONA of reference naphtha 2 (heavier naphtha)

| NAPHTHA | N paraffins | Iso paraffins | N olefins | Iso olefins | Cyclo olefins | naphthenic | aromatics | TOTAL |
|---|---|---|---|---|---|---|---|---|
| 4 | 1.32 | 0.08 | 0.30 | 0.05 | 0.00 | 0.00 | 0.00 | 1.75 |
| 5 | 10.30 | 8.40 | 1.06 | 1.56 | 0.82 | 1.47 | 0.00 | 23.61 |
| 6 | 7.43 | 10.35 | 0.08 | 0.11 | 0.03 | 5.94 | 1.41 | 25.35 |
| 7 | 3.95 | 5.89 | 0.02 | 0.00 | 0.00 | 6.59 | 1.09 | 17.54 |
| 8 | 2.62 | 4.25 | 0.02 | 0.00 | 0.00 | 5.97 | 1.52 | 14.38 |
| 9 | 0.03 | 5.11 | 0.00 | 0.00 | 0.06 | 4.75 | 1.16 | 11.11 |
| 10 | 0.27 | 2.42 | 0.00 | 0.00 | 0.00 | 1.78 | 0.09 | 4.56 |
| 11 | 0.00 | 0.12 | 0.07 | 0.00 | 0.00 | 0.45 | 0.00 | 0.64 |
| 12+ | 0.00 | 0.89 | 0.00 | 0.00 | 0.00 | 0.00 | 0.04 | 0.93 |
| TOTAL | 25.92 | 37.51 | 1.55 | 1.72 | 0.91 | 26.95 | 5.31 | 99.87 |

| | | |
|---|---|---|
| D86: Distillation ASTM D86 T° C. @ IBP | 36.7 | ° C. |
| D86: T° C. @ 50% vol | 83.3 | ° C. |
| D86: T° C. @ FBP | 165.8 | ° C. |
| Density @ 15° C. | 0.7025 | g/ml |

Table 5 shows that naphtha 2 has 17 wt % C9+ whereas naphtha 1 has only 3.3 wt % C9+. Naphtha 2 has therefore a higher content of heavier compounds than naphtha 1. When naphtha 2 is steam cracked, it results in the production of less ethylene and propylene than naphtha 1 under similar operating conditions. Additionally the amount of C9+ heavies produced during steam cracking increases and the heat duty per unit HVC are higher. Naphtha 2 is of poorer quality than naphtha 1 and it is therefore cheaper on the market.

According to the present invention (table 6), when using non-cyclic essentially linear paraffins, having more than 12 carbon atoms, a part of the higher quality naphtha 1 can be replaced by lower quality naphtha 2, while not producing significantly more methane or C9+ heavies. The ethylene/methane ratio is still higher than for the naphtha 1 only and the heat duty per unit HVC remains below that needed for naphtha 1 only.

These examples demonstrate that a technical solution has been discovered for making high value chemicals from biologically produced fatty acids, mono, di or triglycerides by thermochemical treatment to remove most of the oxygen atoms, blend the essentially linear paraffins having more than 12 carbon atoms with fossil naphtha and steam crack the blend under typical conditions used for fossil naphtha only. No excessive amounts of heavies (C9+) are produced under naphtha cracking conditions and ethylene/methane ratios are higher than for fossil naphtha only.

Example 5—Mixtures of Naphtha with a Bio Feed

The hydrodeoxygenation of palm oil of example 3 (hereafter not isomerized bio feed) was also isomerized to get a

TABLE 6

Operating conditions and analysis of the effluents for the steam cracking according to example 4

| | | Naphtha 1 | Naphtha 2 | n-C15 | Naphtha 1/n-C15/Naphtha 2 80/20/0 | Naphtha 1/n-C15/Naphtha 2 60/20/20 |
|---|---|---|---|---|---|---|
| OPERATING CONDITIONS | | | | | | |
| Residence time | s | 0.362 | 0.369 | 0.393 | 0.368 | 0.369 |
| STEAM TO OIL RATIO | KG/KG | 0.30 | 0.30 | 0.30 | 0.30 | 0.30 |
| Coil outlet pressure | BARA | 1.60 | 1.60 | 1.60 | 1.60 | 1.60 |
| Coil outlet temperature | ° C. | 820 | 820 | 820 | 820 | 820 |
| PRODUCT YIELDS | | | | | | |
| CO | WT % | 0.05 | 0.05 | 0.05 | 0.05 | 0.05 |
| CO2 | | 0.00 | 0.00 | 0.00 | 0.00 | 0.00 |
| HYDROGEN | | 0.87 | 0.88 | 0.63 | 0.81 | 0.81 |
| METHANE | | 15.52 | 15.73 | 11.30 | 14.55 | 14.60 |
| ACETYLENE | | 0.28 | 0.28 | 0.31 | 0.28 | 0.28 |
| ETHYLENE | | 26.44 | 24.87 | 36.35 | 28.45 | 28.13 |
| ETHANE | | 4.04 | 3.99 | 6.04 | 4.44 | 4.44 |
| MAPD | | 0.58 | 0.57 | 0.43 | 0.54 | 0.54 |
| PROPYLENE | | 15.87 | 14.95 | 17.08 | 16.17 | 15.98 |
| PROPANE | | 0.48 | 0.49 | 0.68 | 0.52 | 0.52 |
| 1,3-BUTADIENE | | 4.55 | 4.65 | 6.67 | 4.90 | 4.93 |
| 1-BUTENE | | 1.45 | 1.34 | 1.83 | 1.52 | 1.50 |
| ISOBUTENE | | 2.87 | 2.73 | 0.19 | 2.35 | 2.32 |
| 2-BUTENE | | 0.90 | 0.86 | 0.74 | 0.90 | 0.89 |
| ISOBUTANE | | 0.07 | 0.05 | 0.02 | 0.06 | 0.06 |
| NBUTANE | | 0.36 | 0.22 | 0.08 | 0.32 | 0.29 |
| OTHER C4 | | 0.04 | 0.04 | 0.06 | 0.04 | 0.04 |
| C5 CUT | | 4.94 | 4.58 | 3.63 | 4.82 | 4.74 |
| C6 NONARO | | 1.74 | 1.46 | 0.56 | 1.62 | 1.56 |
| BENZENE | | 8.43 | 8.96 | 7.23 | 8.05 | 8.17 |
| C7 NONARO | | 0.41 | 0.42 | 0.18 | 0.40 | 0.40 |
| TOLUENE | | 3.39 | 4.04 | 2.01 | 3.09 | 3.22 |
| C8 NONARO | | 0.04 | 0.08 | 0.03 | 0.04 | 0.05 |
| ETHYLBENZENE/XYLENES | | 0.88 | 1.34 | 0.30 | 0.77 | 0.87 |
| STYRENE | | 0.92 | 1.05 | 0.71 | 0.88 | 0.91 |
| C9+ | | 4.88 | 6.37 | 2.91 | 4.42 | 4.72 |
| HVC | wt % | 56.16 | 54.31 | 67.95 | 58.38 | 58.01 |
| Ultimate HVC | wt % | 59.39 | 57.50 | 72.79 | 61.94 | 61.57 |
| Ethylene/methane ratio | wt %/wt % | 1.70 | 1.58 | 3.22 | 1.96 | 1.93 |
| DUTY RADIATION/HVC | MW/HVC % | 0.473 | 0.485 | 0.459 | 0.469 | 0.471 |

Consequently the invention also allows providing a feedstock for a steam cracker obtained by mixing non-cyclic essentially linear paraffins with usual naphtha and also adding a lower quality naphtha while maintaining the performance of steam cracker or even improving the performance of the steam cracker. The performance of the steam cracker is improved when the HVC content is improved. A similar result would be obtained if naphtha 2 was replaced by a gasoil.

"isomerized bio feed". The isomerization was performed in the presence of Pt/SAPO-11 catalyst on alumina binder at a temperature of 355° C. and under a pressure of 4.0 MPa, using H2/HC ratio of 2000 Nl/L and WHSV 0.5 h$^{-1}$ in a vertical plug flow reactor operated downflow. The gas were stripped from the liquid at the exit of the unit. The main properties of the isomerized product is given in the table below.

TABLE 7

| Main properties of the isomerized bio feed. | | |
| --- | --- | --- |
| Density @ 15° C. | g/ml | 0.7794 |
| Cloud point ASTM D 5771 | ° C. | −21.0 |
| Pour point ASTM D5950 | ° C. | N.D. |
| Kinematic Viscosity ASTM D445 @ 20° C. | mm2/s | 4.536 |
| Kinematic Viscosity ASTM D445 @ 40° C. | mm2/s | 2.911 |
| Cold Filter Plugging point IP 309 | ° C. | −22.0 |

The cloud point of the hydrodeoxygenation of palm oil of example 3 is of 17° C. measured according to ASTM D5771. It was mixed at various concentrations with a light naphtha having a density at 15° C. of 0.6527 g/mL. The hydrodeoxygenation of palm oil of example 3 was also mixed at various concentrations with the same light naphtha. The cloud point values of the various mixture obtained are presented in the tables below.

TABLE 8

| Cloud point values of the mixtures of not isomerized and isomerized bio feeds. | | | | | | | | | |
| --- | --- | --- | --- | --- | --- | --- | --- | --- | --- |
| Bio feed in light naphtha | % wt | 0% | 5% | 10% | 20% | 30% | 40% | 50% | 100% |
| Isomerized bio feed - cloud point ASTM D5771 | ° C. | −42< | −42< | −42< | −42< | −42< | −38 | −35 | −21 |
| Not isomerized bio feed - cloud point ASTM D5771 | ° C. | −42< | −34 | −29 | −17 | −13 | −7 | −6 | 17 |

It appears that with the not isomerized biofeed content in a light naphtha at 50 wt %, the cloud point of the mixture is at −6° C. which is the maximum that may be used in a plant without investing in heaters for storage or for the pipelines.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. As a consequence, all modifications and alterations will occur to others upon reading and understanding the previous description of the invention. In particular, dimensions, materials, and other parameters, given in the above description may vary depending on the needs of the application.

The invention claimed is:

1. A process for the production of high value chemicals, including at least ethylene, propylene, and benzene, and optionally hydrogen, toluene, xylenes and/or 1,3-butadiene by steam cracking comprising:
  (a) providing a non-cyclic paraffin stream (A) comprising at least 90 wt % of paraffins having at least 12 carbon atoms and less than 5 wt % multi-branched paraffins, by mixing a stream (a1) comprising at least 90 wt % of linear paraffins with a stream (a2) comprising at least 30 wt % of ramified paraffins, wherein the non-cyclic paraffin stream (A) is biologically produced,
  (b) providing a hydrocarbon stream (B) comprising at least 90 wt % of components having a boiling point ranging from 15° C. to 200° C. measured by ASTM D86 or at least 90 wt % of hydrocarbons having from 3 to 4 carbon atoms,
  (c) mixing the non-cyclic paraffin stream (A) with the hydrocarbon stream (B) to form a feedstock mixture; wherein a weight content of the non-cyclic paraffin stream (A) in the feedstock mixture is at least 10 wt % and lower than 75 wt %,
  (d) steam cracking the feedstock mixture with steam in a reactor to obtain cracking products including at least ethylene, propylene and benzene, and optionally hydrogen, toluene, xylenes and 1,3-butadiene; wherein the step (d) is carried out at a steam to hydrocarbon weight ratio that is less than 0.5 and at a coil outlet temperature of at least 820° C., and
  (e) conducing another steam cracking of another feedstock mixture with steam in the reactor without changing the stream to hydrocarbon weight ratio or the coil outlet temperature, thereby increasing an amount of ethylene and propylene in cracking products of the another steam cracking compared to the cracking products obtained in the step (d), wherein the another feedstock mixture is obtained by increasing an amount of the non-cyclic paraffin stream (A) in the feedstock mixture and adding at least one hydrocarbon stream (B*) to the feedstock mixture, wherein the at least one hydrocarbon stream (B*) is a naphtha or a gasoil having an initial boiling point, IBP, of at least 2° C. higher than the hydrocarbon stream (B) and a final boiling point, FBP, of at least 5° C. higher than the hydrocarbon stream (B).

2. The process according to claim 1 wherein a weight content of linear paraffins originating from the non-cyclic paraffin stream (A) in the feedstock mixture obtained in the step (c) is at most 50 wt %.

3. The process according to claim 1 wherein the stream (a2) is obtained by isomerizing a part of the stream (a1).

4. The process according to claim 1 wherein the non-cyclic paraffin stream (A) further comprises at least 30 wt % of linear paraffins and/or less than 5 wt % multiple-branched paraffins, the rest of the composition being single branched paraffins.

5. The process according to claim 1 wherein the coil outlet temperature ranges from 820 to 875° C. or a residence time of the steam cracking in the step (d) and the another steam cracking in the step (e) ranges from 0.05 to 0.5 seconds.

6. The process according to claim 1 wherein the feedstock mixture in the step (d) and the another feedstock mixture in the step (e) is mixed with steam in a ratio of 0.35 to 0.45 kg steam per kg of feedstock mixture.

7. The process according to claim 1, further comprising obtaining stream (a1) of the non-cyclic paraffin stream (A) by catalytic hydrodeoxygenation or catalytic decarbonylation or decarboxylation of fatty acids or mono-, di- or triglycerides thereof, or thermal decarboxylation of fatty acids soaps, the fatty acids having at least 12 carbon atoms and wherein the hydrodeoxygenation or catalytic decarbonylation or decarboxylation are being performed in the presence of other hydrocarbons in a boiling range of 15° C. to 350° C. as measured by ASTM D86.

8. The process according to claim 7 wherein the catalytic hydrodeoxygenation or the catalytic decarbonylation or decarboxylation of fatty acids or mono-, di- or triglycerides thereof is carried out in the presence of hydrogen and of at least one catalyst that can be selected among Ni, Mo, Co, NiW, NiMo, CoMo, NiCoW, NiCoMo, NiMoW and CoMoW oxides or sulphides as catalytic phase, wherein the catalyst is supported on high surface area carbon, alumina, silica, titania or zirconia and mixtures thereof.

9. The process according to claim 7, further comprising producing stream (a1) of the non-cyclic paraffin stream (A) by:
(i) hydrolysis of the fats and oils into glycerol and fatty acids, followed by removal of the glycerol, or (ii) physical refining, including a steam distillation or vacuum distillation of fats and oils, or (iii) acidulation of soaps, and
catalytic hydrodeoxygenation or catalytic decarbonylation or decarboxylation of the fatty acids, the catalytic hydrodeoxygenation or catalytic decarbonylation or decarboxylation being conducted in the presence of hydrogen and of at least one catalyst that can be selected among Ni, Mo, Co, NiW, NiMo, CoMo, NiCoW, NiCoMo, NiMoW and CoMoW oxides or sulphides as catalytic phase, wherein the catalyst is supported on high surface area carbon, alumina, silica, titania or zirconia and mixtures thereof or group 10 and group 11 metals or alloy mixtures supported on high surface area carbon, magnesia, zinc oxide, spinels, perovskites, calcium silicates, alumina, silica or silica-aluminas or mixtures of the latter.

10. The process according to claim 7, further comprising producing stream (a1) of the non-cyclic paraffin stream (A) by:
(i) hydrolysis of the fats and oils into glycerol and fatty acids, followed by removal of the glycerol, or (ii) physical refining, including a steam distillation or vacuum distillation of fats and oils, or (iii) acidulation of soaps, and
thermal decarboxylation of the fatty acids soaps which is carried out on basic oxides, spinels, perovskites, calcium silicates, either as bulk material or dispersed on neutral or basic carriers.

11. The process according to claim 7 wherein:
the catalytic hydrodeoxygenation is carried out at a temperature from 200 to 500° C., under a pressure from 1 MPa to 10 MPa (10 to 100 bars) and with a hydrogen to feedstock ratio from 100 to 2000 NL/L, or wherein the catalytic decarbonylation or decarboxylation is carried out at a temperature from 100 to 550° C., under a pressure from 0.1 MPa to 10 MPa (1 to 100 bars) and with a hydrogen to feedstock ratio from 0 to 2000 NL/L.

12. The process of claim 7, wherein the other hydrocarbons comprise fossil naphtha, gasoil, or a combination thereof.

13. The process according to claim 1, wherein the hydrocarbon stream (B) comprises a mixture of a first hydrocarbon stream and a second hydrocarbon stream, wherein the first hydrocarbon stream comprises less than or equal to 5 wt % of hydrocarbons having more than 9 carbon atoms (C9+), and wherein the second hydrocarbon stream comprises greater than 10 weight percent (wt %) of hydrocarbons having more than 9 carbon atoms (C9+).

14. A process for the production of high value chemicals, including at least ethylene, propylene, and benzene, and optionally hydrogen, toluene, xylenes and/or 1,3-butadiene by steam cracking comprising:

(a) steam cracking a hydrocarbon stream comprising at least 90 wt % of components having a boiling point ranging from 15° C. to 200° C. measured by ASTM D86 in a reactor to obtain cracking a cracking product including at least ethylene, propylene and benzene, and optionally hydrogen, toluene, xylenes and 1,3-butadiene, wherein the steam cracking is effected at a steam to hydrocarbon weight ratio and a coil outlet temperature; and
(b) conducting another steam cracking of a feedstock mixture in a reactor thereby obtaining another cracking product comprising an increased amount of ethylene and propylene relative to the amount of ethylene and propylene in the cracking product obtained in the step (a), wherein the feedstock mixture is obtained by mixing the hydrocarbon stream with a non-cyclic paraffin stream and at least one additional hydrocarbon stream, wherein the non-cyclic paraffin stream comprises at least 90 wt % of paraffins having at least 12 carbon atoms and less than 5 wt % multi-branched paraffins, wherein the at least one additional hydrocarbon stream is a naphtha or a gasoil having an initial boiling, IBP, of at least 2° C. higher than the hydrocarbon stream and a final boiling point, FBP, of at least 5° C. higher than the hydrocarbon stream, wherein the non-cyclic paraffin stream is obtained by mixing a stream (a1) comprising at least 90 wt % of linear paraffins with a stream (a2) comprising at least 30 wt % of ramified paraffins, and wherein a weight content of the non-cyclic paraffin stream in the feedstock mixture is at least 10 wt % and lower than 75 wt %, and wherein the non-cyclic paraffin stream is biologically produced; and the another steam cracking of the feedstock mixture is conducted at a steam to hydrocarbon weight ratio that is less than 110% of the steam to hydrocarbon weight ratio of in the step (a) and at a coil outlet temperature that is less than 102% of the coil outlet temperature of the step (a) to obtain the another cracking product, wherein the another cracking product includes at least ethylene, propylene and benzene, and optionally hydrogen, toluene, xylenes and 1,3-butadiene.

15. The process of claim 14, wherein the another cracking product obtained in the step (b) comprise less methane and hydrocarbons having more than 9 carbon atoms (C9+) than the cracking product obtained in the step (a).

16. The process of claim 14, wherein the hydrocarbon stream in the step (a) comprises less than or equal to 5 wt % of C9+ hydrocarbons, and wherein the process further comprises introducing a hydrocarbon stream comprising greater than 10 weight percent (wt %) C9+ hydrocarbons into the feedstock mixture in the step (b).

17. The process of claim 1, wherein the hydrocarbon stream (B) comprises at least 90 wt % of hydrocarbons having from 3 to 4 carbon atoms.

18. The process according to claim 14, wherein a weight content of the non-cyclic paraffin stream in the feedstock mixture is greater than 20 wt %.

19. The process according to claim 1, wherein the amount of the non-cyclic paraffin stream (A) in the another feedstock mixture is greater than 20 wt %.

20. The process of claim 1, wherein the hydrocarbon stream (B) and the at least one hydrocarbon stream (B*) comprise naphtha.

* * * * *